(12) United States Patent
Gefroh et al.

(10) Patent No.: US 10,583,397 B2
(45) Date of Patent: Mar. 10, 2020

(54) PROCESS CONTROL SYSTEMS AND METHODS FOR USE WITH FILTERS AND FILTRATION PROCESSES

(71) Applicant: AMGEN INC., Thousand Oaks, CA (US)

(72) Inventors: Eva Gefroh, Newcastle, WA (US); Randolph W. Schweickart, Woodinville, WA (US); Krista Petty, Newbury Park, CA (US); Gregory Frank, Thousand Oaks, CA (US); Christine Salstrom Terpsma, Kenmore, WA (US); Arthur C. Hewig, III, Newbury Park, CA (US); Joseph Edward Shultz, Binningen (CH)

(73) Assignee: AMGEN INC., Thousand Oaks, CA (US)

( * ) Notice: Subject to any disclaimer, the term of this patent is extended or adjusted under 35 U.S.C. 154(b) by 76 days.

(21) Appl. No.: 15/302,762

(22) PCT Filed: May 13, 2015

(86) PCT No.: PCT/US2015/030599
§ 371 (c)(1),
(2) Date: Oct. 7, 2016

(87) PCT Pub. No.: WO2015/175679
PCT Pub. Date: Nov. 19, 2015

(65) Prior Publication Data
US 2017/0157566 A1  Jun. 8, 2017

Related U.S. Application Data

(60) Provisional application No. 61/992,595, filed on May 13, 2014.

(51) Int. Cl.
*B01D 61/22* (2006.01)
*B01D 61/18* (2006.01)
(Continued)

(52) U.S. Cl.
CPC ........... *B01D 61/22* (2013.01); *B01D 61/142* (2013.01); *B01D 61/145* (2013.01); *B01D 61/18* (2013.01);
(Continued)

(58) Field of Classification Search
CPC .... B01D 61/14; B01D 61/142; B01D 61/145; B01D 61/18; B01D 61/22; B01D 2311/04;
(Continued)

(56) References Cited

U.S. PATENT DOCUMENTS 5,164,092 A * 11/1992 Munch ................. B01D 61/142
210/321.64
5,252,350 A  10/1993 Hartmann
(Continued)

FOREIGN PATENT DOCUMENTS

CN  102276074 A  12/2011
EP   1623752 A2   2/2006
(Continued)

OTHER PUBLICATIONS

International Preliminary Report on Patentability and Written Opinion for PCT/US2015/030599, dated Nov. 15, 2016.
(Continued)

*Primary Examiner* — Joseph W Drodge
(74) *Attorney, Agent, or Firm* — Marshall, Gerstein & Borun LLP

(57) ABSTRACT

Systems and methods used to control tangential flow filtration are provided, including control systems and methods for use with connected systems with upstream processing units,
(Continued)

such as chromatography processing units, in fluid communication with a tangential flow filtration processing unit. Also included are control systems and methods for performing continuous concentration using single-pass tangential flow filtration with permeate flow control.

19 Claims, 21 Drawing Sheets

(51) Int. Cl.
  *C07K 1/34* (2006.01)
  *B01D 61/14* (2006.01)
(52) U.S. Cl.
  CPC ............ *C07K 1/34* (2013.01); *B01D 2311/04* (2013.01); *B01D 2311/06* (2013.01); *B01D 2313/243* (2013.01); *B01D 2315/10* (2013.01)
(58) Field of Classification Search
  CPC ............ B01D 2311/06; B01D 2311/16; B01D 2311/2626; B01D 2311/2649; B01D 2313/18; B01D 2313/243; B01D 2315/10; B01D 61/10; B01D 61/12; B01D 61/20; C07K 1/34; C07K 1/36; C12M 29/04; C02F 1/008; C02F 1/44; C02F 1/442; C02F 1/444; C02F 2209/40; C02F 2209/44
  USPC ........... 210/650, 651, 739, 87, 97, 137, 143, 210/321.6, 321.65, 637
  See application file for complete search history.

(56) References Cited

U.S. PATENT DOCUMENTS

| | | | | |
|---|---|---|---|---|
| 5,490,937 A * | 2/1996 | van Reis | ............... | B01D 61/142 210/637 |
| 5,589,076 A * | 12/1996 | Womack | ................ | B01D 37/02 210/739 |
| 5,843,298 A * | 12/1998 | Orac | ......................... | C10C 1/00 208/42 |
| 6,074,551 A * | 6/2000 | Jones | .................... | B01D 61/025 210/106 |
| 6,168,714 B1 * | 1/2001 | Ilias | ........................ | B01D 61/02 210/195.2 |
| 6,296,770 B1 * | 10/2001 | Wilcox | ................ | B01D 61/147 210/195.2 |
| 7,410,587 B2 | 8/2008 | Schick | | |
| 9,452,451 B2 * | 9/2016 | Kleiner | ...................... | B08B 1/04 |
| 2002/0043487 A1 * | 4/2002 | Schick | ................ | B01D 61/145 210/85 |
| 2002/0195152 A1 * | 12/2002 | Fernandes | ......... | B01L 3/502707 137/803 |
| 2004/0110931 A1 * | 6/2004 | Holten | ................ | C07K 16/065 530/388.1 |
| 2004/0167320 A1 | 8/2004 | Couto et al. | | |
| 2005/0023194 A1 | 2/2005 | Petersen et al. | | |
| 2005/0197496 A1 * | 9/2005 | Perreault | .................. | C07K 1/34 530/412 |
| 2005/0224412 A1 * | 10/2005 | Best | ..................... | B01D 61/142 210/637 |
| 2006/0051347 A1 | 3/2006 | Winter | | |
| 2007/0151925 A1 * | 7/2007 | de los Reyes | ......... | B01D 61/14 210/641 |
| 2007/0163628 A1 * | 7/2007 | Zimmer | .................. | A23L 2/082 134/134 |
| 2007/0235889 A1 * | 10/2007 | Hartounian | .......... | A61K 9/1277 264/4.1 |
| 2007/0246406 A1 * | 10/2007 | Dibel | ................... | B01D 61/142 210/96.2 |
| 2009/0120873 A1 * | 5/2009 | Becker | .................... | B01D 61/14 210/636 |
| 2012/0125846 A1 * | 5/2012 | Suzumura | .............. | B01D 61/14 210/637 |
| 2012/0301903 A1 * | 11/2012 | Putnam | .................. | G01N 21/05 435/7.92 |
| 2013/0001142 A1 * | 1/2013 | Novak | .................... | C02F 3/006 210/96.2 |
| 2013/0239666 A1 | 9/2013 | Carpenter et al. | | |
| 2013/0345402 A1 | 12/2013 | Vogel et al. | | |
| 2014/0048462 A1 * | 2/2014 | Cohen | .................... | B01D 61/22 210/96.2 |
| 2014/0187751 A1 * | 7/2014 | Nti-Gyabaah | ........... | C07K 1/36 530/387.3 |
| 2015/0158907 A1 * | 6/2015 | Zhou | ...................... | C12M 29/04 435/183 |
| 2016/0176921 A1 * | 6/2016 | Rajendran | ................ | C07K 1/36 530/387.3 |

FOREIGN PATENT DOCUMENTS

| | | |
|---|---|---|
| EP | 2119492 A1 | 11/2009 |
| GB | 2348155 A | 9/2000 |
| JP | H03143382 A | 6/1991 |
| JP | H1033957 A | 2/1998 |
| JP | S63252505 A | 10/1998 |
| WO | WO-2004004873 A1 | 1/2004 |
| WO | WO-2012032354 A1 | 3/2012 |

OTHER PUBLICATIONS

International Search Report for PCT/US2015/030599, dated Nov. 19, 2015.
Written Opinion for Singapore Application No. 11201608998V, dated Jul. 11, 2018.
Japanese Patent Application No. 2016-567603, Office Action, dated Jun. 11, 2019.
Australian Patent Application No. 2015259228, Examination Report No. 1, dated Mar. 29, 2019.
Chilean Patent Application No. 02875-2016, Examination Report, dated Feb. 13, 2019.
Chinese Patent Application No. 201580024939.4, First Office Action, dated Jan. 28, 2019.
Eurasian Patent Application No. 201692277, Office Action, dated Oct. 26, 2018.
Eurasian Patent Application No. 201692277/31, Office Action, dated Jan. 31, 2018.
European Patent Application No. 15727133.9, Communication Pursuant to Article 94(3) EPC, dated Apr. 20, 2018.
Singapore Patent Application No. 11201608998V, Search Report, dated Nov. 1, 2017.
Singapore Patent Application No. 11201608998V, Written Opinion, dated Jun. 29, 2018.
European Patent Application No. 15727133.9, Communication Pursuant to Article 94(3) EPC, dated Aug. 7, 2019.
Chinese Patent Application No. 201580024939.4, Second Office Action, dated Sep. 20, 2019.
Indian Patent Application No. 201617041890, Examination Report, dated Nov. 21, 2019.
Singapore Patent Application No. 11201608998V, Written Opinion, dated Oct. 10, 2019.

* cited by examiner

Table 1. TFF Control Strategies for a Connected Downstream Process

| Strategy | Inlet Flow | Permeate Flow | Tank Volume | Feed Crossflow |
|---|---|---|---|---|
| Variable Flow Strategy | Variable (↓ with flux) | Variable (matched) | Constant | Constant (maximum crossflow) |
| Constant Flow Strategy | Constant | Constant | Constant | Variable (controls flux) |
| Surge Strategy | Constant | Variable | Variable (surge) | Constant (maximum crossflow) |

FIG. 13

Table 2. Examples of Developed Connected Processes

| Process parameters | | Units | CEX-AEX(FT)-VF-UF | CEX-HIC(FT)-VF-UF | CEX-VF-UF | HIC(BE)-VF-UF | HIC(FT)-VF-UF |
|---|---|---|---|---|---|---|---|
| Molecule | | | (mAb A) | (mAb B) | (mAb C) | (mAb D) | (mAb E) |
| CEX or HIC (BE) | Size | cm-D | | 60 | 60 | 80 | |
| | Load capacity | g/$L_r$ | 80 | 80 | 80 | 35 | NA |
| | Linear flow | cm/hr | 140 | 140 | 120 | 90 | |
| Inline titration | % dilution | % v/v | NA | 20% | NA | NA | 18% |
| AEX (FT) membrane or HIC (FT) | Size | cm-D | 180 mL | 60 | NA | NA | 60 |
| | Loading | g/$L_r$ | 10.7 kg/$L_m$ | 72 | | | 104 |
| | Linear flow | cm/hr | 16.3 MV/min | 174 | | | 180 |
| VF | Filter area | $m^2$ | 1.0 | 1.5 | 1.0 | 1.0 | 2.0 |
| | Loading | g/$m^2$ | 1900 | 2550 | 4210 | 3670 | 3430 |
| | Filtrate flux | LMH | 172 | 320 | 333 | 444 | 249 |
| UF | Filter area | $m^2$ | 4.6 | 9.1 | 9.1 | 9.1 | 16 |
| | Loading | g/$m^2$ | 412 | 421 | 471 | 410 | 438 |
| | Perm. flux | LMH | 39 | 54 | 38 | 50 | 32 |
| | UF1a conc.* | g/L | 40 | 38 | 37 | 26 | 47 |
| Yield | | | 94% | 82% | 89% | 80% | 89% |

* UF1a conc. refers to the concentration in the retentate tank at the end of the connected phase when all the mass has accumulated in the tank

FIG. 20

PROCESS CONTROL SYSTEMS AND METHODS FOR USE WITH FILTERS AND FILTRATION PROCESSES

CROSS REFERENCE

This is the United States national phase of International Patent Application No. PCT/US15/30599, having an international filing date of May 13, 2015, and which claims the priority benefit of U.S. Provisional Application No. 61/992,595, filed May 13, 2014. The contents of each of the foregoing is expressly incorporated herein by reference in the entirety.

BACKGROUND

This patent is directed to process control systems and methods, and, in particular, to process control systems and methods for use with filters and filtration processes.

Many products—for example antibodies, and more particularly monoclonal antibodies—are derived from cells. To prepare a cell-derived product, one or more initial unit operations may be performed to remove the cells and any associated cell debris to enable purification. After purification, one or more subsequent unit operations may be performed to prepare the product for administration. Filtration may be included both in the initial and subsequent unit operations, as will be explained below in the context of a general description of the overall process of preparing a cell-derived product.

With reference to commercial-scale unit operations that may be used to prepare a therapeutic-grade extracelluarly-expressed product, such as an antibody or immunoglobulin, an initial separation operation such as centrifugation or filtration may be used to remove cells and cell debris. Centrifugation involves the application of centrifugal force (relative to an axis) to a liquid solution or suspension to cause more-dense components of the solution or suspension to migrate further away from the axis, and less-dense components of the solution or suspension to migrate toward the axis (or at least to migrate less further away from the axis than the more-dense components). Filtration is pressure-driven process that uses membranes to separate components in a liquid solution or suspension according to size differences between the components. When used in a cell separation harvest application, the filtration may be referred to as microfiltration. Either the centrifugation or the filtration referred to above may be preceded by or followed with one or more (additional) filtration unit operations, depending on the amount of cell and/or cell debris initially in the solution or suspension or on the degree to which centrifugation or the primary filtration process has separated out the cells and/or cell debris.

Once the cells and cell debris have been satisfactorily removed, purification may be performed in one or more devices (which may be in the form of one or more columns) using a process known as chromatography. Chromatography involves the interaction between a first phase, referred to as the mobile phase, and a second phase, referred to as the stationary phase. Oftentimes, the product of interest in the mobile phase binds to the stationary phase, and then a solvent (referred to as an eluent) is used to separate the product from the stationary phase. Other times, the product of interest flows through in the mobile phase, while contaminants bind to the stationary phase.

The exact nature of the interaction between the mobile and stationary phases differs with the type of chromatography used. Ion exchange chromatography relies on the forces of attraction between charged molecules of the product of interest (or contaminant) and an oppositely-charged solid phase. For example, in cation exchange chromatography, positively-charged molecules are attracted to a negatively-charged solid phase. Affinity chromatography involves the use of a ligand that specifically binds to the product (i.e., the target molecule) or the contaminant. In regard to an antibody or immunoglobulin product of interest, the ligand may be the associated antigen.

Once purification has been completed, the product that is eluted from the chromatography device may be transported for further processing prior to administration to the patient including for example, formulating the protein in a pharmaceutically acceptable excipient and/or performing filtration. For example, filtration may be performed to remove any viruses present to ensure the virus safety of the biotech-derived therapeutic. Additionally, filtration may be performed on the product to concentrate the product to therapeutic levels and to desalt the product. While the object of the filtration is still to separate larger components from smaller components, unlike the pre-purification filtration performed to remove cell and cell debris from the product, the post-purification filtration removes small peptides and salts from the product so as to increase the concentration of the product. This filtration may also be used to desalt the product, or to introduce a stable drug substance formulation for storage of the product prior to filling (i.e., buffer exchange or replacement). When used in this context, the filtration may be referred to as ultrafiltration.

The filtration described above may be a dead-end process or a crossflow, or tangential flow, process. In a dead-end filter, the flow of the liquid solution or suspension to be separated (or feed) is perpendicular to the membrane. The majority of the feed flow in a crossflow filter is tangential to or across the surface of the membrane.

Tangential flow filtration (or TFF) provides certain advantages to dead-end filtration. In particular, the material that builds up on the membrane surface (also referred to as a stagnant film layer) is minimized during tangential flow filtration, increasing the length of time that a filter can be operational. Consequently, tangential flow filtration may be applied to continuous process applications, in that feed may be continuously fed into and through the filter.

A particular type of tangential flow filtration, referred to as single-pass tangential flow filtration (or SPTFF), may be used in certain applications. While conventional TFF involves directing the feed flow in multiple passes through the filter device (or multiple filter devices arranged in parallel), SPTFF involves directing the feed flow through the filter device in a single pass. According to certain embodiments, the SPTFF filter device may include a single membrane. According to other embodiments, the SPTFF filter device may be defined by a plurality of membrane cassettes connected in series, the retentate of one stage directed into the successive stage as the feed flow. The cassettes may be connected with multiple holders or flow diverter plates. Alternatively, a housing may be designed to receive a plurality of membranes, the housing providing paths for connecting the individual membranes.

As set out in detail below, this disclosure sets forth improved process control systems and methods for filters and filtration, and in particular tangential flow filters and filtration, embodying advantageous alternatives to the conventional devices and methods.

SUMMARY

According to an aspect of this disclosure, a process control system includes one or more upstream processing units, each operating a flow rate, a tank connected to the one or more upstream processing units, a filter having an inlet, a permeate outlet and a retentate outlet connected to the tank, a feed pump having an inlet connected to the tank and an outlet connected to the inlet of the filter, and a sensor disposed at the permeate outlet to determine a flow rate at the permeate outlet. The system also includes a control system that is coupled to the sensor and the upstream processes, and adapted to control the flow rate of one or more of the one or more upstream processing units according to the flow rate at the permeate outlet.

According to another aspect of this disclosure, a process control method is provided for use with one or more upstream processing units, a tank connected to the one or more upstream processing units, and a tangential flow filter having an inlet, a permeate outlet and a retentate outlet connected to the tank. The method includes sensing a flow rate at the permeate outlet, and controlling a flow rate of one or more of the one or more upstream processing units according to the flow rate at the permeate outlet.

According to yet another aspect of this disclosure, a process control system includes one or more upstream processing units, each operating a flow rate, a tank connected to the one or more upstream processing units, a filter having an inlet, a permeate outlet and a retentate outlet connected to the tank, a feed pump having an inlet connected to the tank and an outlet connected to the inlet of the filter, and a sensor disposed at the permeate outlet to determine a flow rate at the permeate outlet. The system also includes a control system that is coupled to the sensor and the feed pump, and adapted to control the feed pump according to the flow rate at the permeate outlet.

According to a further aspect of this disclosure, a process control method is provided for use with one or more upstream processing units, a tank connected to the one or more upstream processing units, and a tangential flow filter having an inlet, a permeate outlet and a retentate outlet connected to the tank. The method includes sensing a flow rate at the permeate outlet, and pumping material from the tank into the filter according to the flow rate at the permeate outlet.

According to a still further aspect of this disclosure, a process control system includes one or more upstream processing units, each operating a flow rate, a tank connected to the one or more upstream processing units, a filter having an inlet, a permeate outlet and a retentate outlet connected to the tank, a feed pump having an inlet connected to the tank and an outlet connected to the inlet of the filter, and a sensor disposed at the permeate outlet to determine a flow rate at the permeate outlet. The system also includes a control system that is coupled to the sensor and the feed pump, and adapted to control the feed pump according to the flow rate at the permeate outlet until a predetermined flow rate is reached for the feed pump, and to control the flow rate of one or more of the one or more upstream processing units according to the flow rate at the permeate outlet after the predetermined flow rate is reached for the feed pump.

According to another aspect of this disclosure, a process control method is provided for use with one or more upstream processing units, a tank connected to the one or more upstream processing units, each upstream processing unit having a flow rate, and a filter having an inlet, a permeate outlet and a retentate outlet connected to the tank. The method includes sensing a flow rate at the permeate outlet, pumping material from the tank into the filter according to a flow rate at the permeate outlet until a predetermined pumping flow rate is reached, and subsequently controlling the flow rate of one or more of the one or more upstream processing units once the predetermined pumping flow rate is reached.

According to yet another aspect of this disclosure, a process control system includes one or more upstream processing units, each operating a flow rate, a tank connected to the one or more upstream processing units, a filter having an inlet, a permeate outlet and a retentate outlet connected to the tank, a feed pump having an inlet connected to the tank and an outlet connected to the inlet of the filter, and a sensor disposed at the permeate outlet to determine a flow rate at the permeate outlet. The system also includes a control system that is coupled to the sensor and the feed pump, and adapted to control the feed pump according to the flow rate at the permeate outlet until a predetermined flow rate is reached for the feed pump, and to permit a mismatch between the flow rate of the one or more upstream processing units and the flow rate of the feed pump after the predetermined flow rate is reached for the feed pump.

According to a further aspect of this disclosure, a process control method is provided for use with one or more upstream processing units, a tank connected to the one or more upstream processing units, and a filter having an inlet, a permeate outlet and a retentate outlet connected to the tank. The method includes sensing a flow rate at the permeate outlet, pumping material from the tank into the filter according to the flow rate at the permeate outlet until a predetermined pumping flow rate is reached, and subsequently pumping material from the tank into the filter to according to the predetermined pumping flow rate thereby permitting the volume in the tank to vary.

According to a still further aspect of this disclosure, a process control system includes a microfiltration unit, a single-pass tangential flow filter having an inlet, a permeate outlet and a retentate outlet, a feed pump with an inlet connected to the microfiltration unit and an outlet connected to the inlet of the filter, and a permeate pump with an inlet connected to the permeate outlet of the filter. The system also includes a control system coupled to the permeate pump and adapted to control the permeate pump to vary a flow reduction factor, where the flow reduction factor is the ratio of feed flow to retentate flow.

According to another aspect of this disclosure, a process control method includes pumping material through a single-pass tangential flow filter having an inlet, a permeate outlet and a retentate outlet, and pumping permeate from the permeate outlet of the filter to vary a flow reduction factor, where the flow reduction factor is the ratio of feed flow to retentate flow.

According to another aspect of the disclosure, a process of purifying a protein is provided. The process utilizes one or more upstream processing units, a tank connected to the one or more upstream processing units, and a tangential flow filter having an inlet, a permeate outlet and a retentate outlet connected to the tank. The process includes sensing a flow rate at the permeate outlet while the protein flows from the retentate outlet back to the tank. Then, the process includes performing one of (i) through (iv). According to (i), the process can include controlling a flow rate of one or more of the one or more upstream processing units according to the flow rate at the permeate outlet, the flow rate being a flow rate of a material at least partly including the protein. According to (ii), the process can include pumping a material at least partly including the protein from the tank into the filter according to the flow rate at the permeate outlet. According to (iii), the process can include pumping a material at least partly including the protein from the tank into the filter according to a flow rate at the permeate outlet until a predetermined pumping flow rate is reached, and subsequently controlling the flow rate of one or more of the one or more upstream processing units once the predetermined pumping flow rate is reached. According to (iv), the process can include pumping a material at least partly including the protein from the tank into the filter according to the flow rate at the permeate outlet until a predetermined pumping flow rate is reached, and subsequently pumping material from the tank into the filter to according to the predetermined pumping flow rate thereby permitting the volume in the tank to vary. Finally, after any one of (i) through (iv), the process includes purifying the protein in an eluate, and optionally formulating the protein in a pharmaceutically acceptable excipient.

BRIEF DESCRIPTION OF THE DRAWINGS

It is believed that this disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 13 is a table presenting TFF Control Strategies for a Connected Downstream Process;

FIG. 20 presents a table of examples of developed connected processes;

DETAILED DESCRIPTION OF VARIOUS EMBODIMENTS

Figure 1:
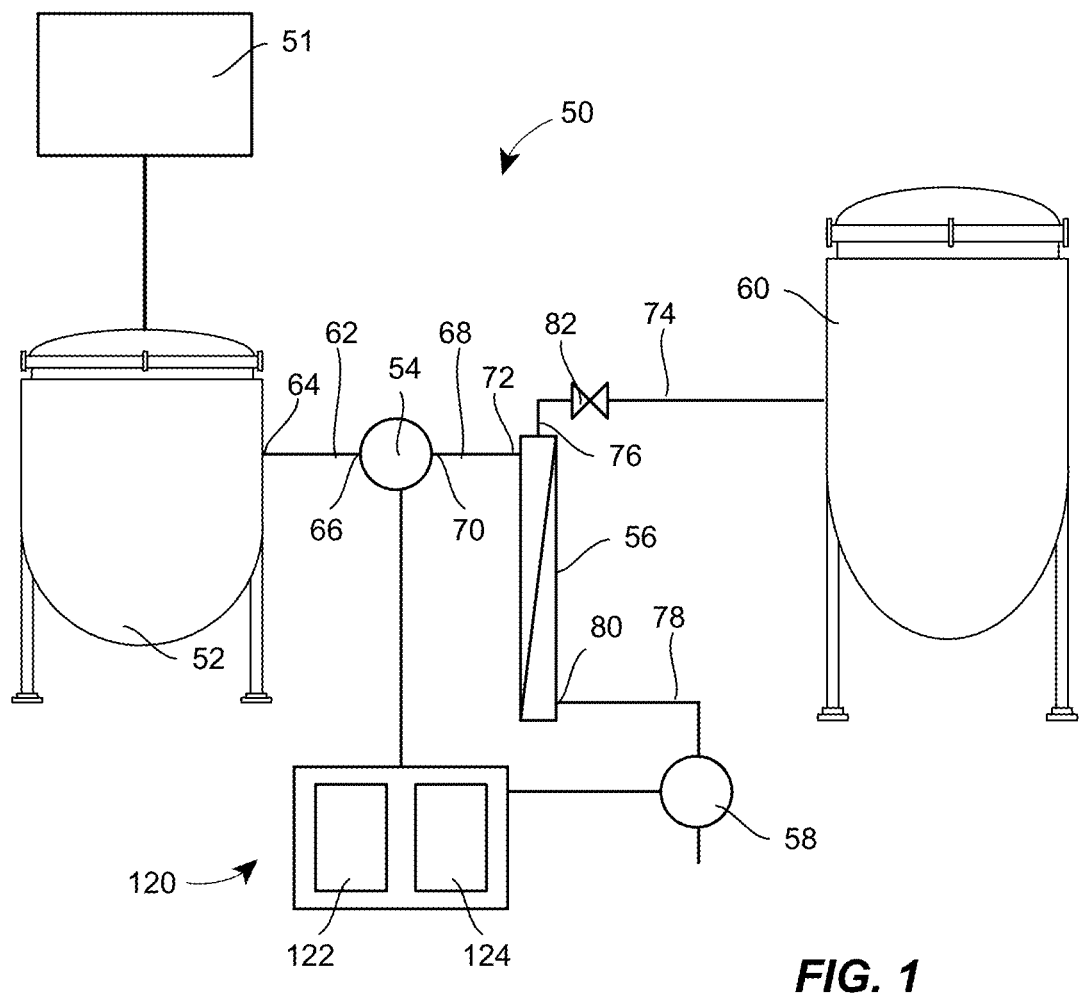
FIG. 1 is a schematic diagram of a control system used in combination with continuous single-pass tangential flow filtration (SPTFF)

This disclosure uses the following terms, for which definitions are provided below:

Filtration: A pressure-driven separation process that uses membranes to separate components in a liquid solution or suspension according to size differences between the components.

Feed: The liquid solution or suspension entering the filter.

Filtrate: The component or components that pass through the membrane. Also referred to as permeate.

Retentate: The component or components that do not pass through the membrane, but instead are retained by the membrane.

Tangential Flow Filtration (TFF): In TFF, the liquid solution or suspension is pumped tangentially along the surface of the membrane. Also referred to as cross-flow filtration.

Single-Pass Tangential Flow Filtration (SPTFF): A type of TFF where the feed flow is directed through the filter device in a single pass without recirculation.

Microfiltration: Filtration used to separate intact cells and relative large cell debris/lysates from the remainder of the components, such as colloidal material, proteins (including the product of interest) and salts. Membrane pore sizes for this type of separation may be in the range of 0.05 µm to 1.0 µm, for example. The filtrate or permeate from the microfiltration process may be referred to as microfiltration harvest fluid.

Ultrafiltration: Filtration used to separate proteins (including the product of interest) from, e.g., relatively small peptides and buffer components, such as in desalting or concentration. Membrane ratings for this type of separation may be expressed in nominal molecular weight limits, and may be in the range of 1 kD to 1000 kD, for example.

Diafiltration: Filtration process that can be performed in combination with the other categories of separation to enhance, for example, product yield or purity. A buffer is introduced into the recycle tank while filtrate is removed from the unit operation.

Transmembrane Pressure (TMP): TMP is the average applied pressure from the feed to the filtrate side of the membrane.

Connected Processes: An upstream process and a downstream process are connected where the downstream process is used concurrently with the upstream process. That is, the operation of the upstream and downstream processes at least overlap temporally.

This disclosure relates to various process control methods and systems for filters and filtration systems. Initially, process control methods and systems are described for concentration of microfiltration harvest fluid using single-pass tangential flow filtration with filtrate (permeate) flow control. Additionally, process control methods and system are described herein for the operation of the ultrafiltration element that is used concurrently (i.e., connected) with one or more upstream unit operations.

As mentioned above, microfiltration is used to separate cells and cell debris from the product of interest. In particular, a microfiltration element is disposed in-line with the harvest stream from the bioreactor. The microfiltration element returns the cell and cell debris to the bioreactor, while the filtrate is collected for further downstream processing.

Microfiltration may be combined with diafiltration to enhance product yield. However, diafiltration increases the liquid volume of filtrate that is collected from the microfiltration element. To obtain a product yield of greater than 80-90%, the liquid volume of filtrate collected from the microfiltration element may be at least three times the working volume of the bioreactor. The sizable amount of liquid volume collected may limit the utility of diafiltration as scale increases.

To permit the use of diafiltration with microfiltration to enhance product yields in large-scale operations, process control methods and systems are described herein for concentration of the permeate from the microfiltration element (referred to herein as microfiltration harvest fluid). In particular, these process control methods and systems use single-pass tangential flow filtration (SPTFF) with permeate flow control.

During the operation of the microfiltration in a constant volume diafiltration mode, the product concentration starts out high due to the accumulation of product in the bioreactor during the production phase. That is, the product concentration starts out high because there has been no removal of product as yet, and buffer has not yet been added as part of the diafiltration process. The product concentration in the bioreactor (and in the filtrate of the microfiltration element) will decrease as product passes through the microfiltration element and media is added as part of the diafiltration process. The changing product concentration would have an effect on the use of SPTFF downstream to concentrate the microfiltration harvest fluid because SPTFF conversion of feed to permeate is dependent on the feed concentration as well as the cross-flow rate and transmembrane pressure. A changing product concentration in the microfiltration element filtrate would result in changing conversion of feed to permeate in the SPTFF.

According to this disclosure, single-pass tangential flow filtration (SPTFF) is used in combination with a control system and method to achieve concentration of microfiltration harvest fluid.

As to the hardware, FIG. 1 illustrates a processing system 50 including a microfiltration unit 51, an optional first tank 52 that receives the filtrate from microfiltration unit 51, a feed pump 54 (which according to other embodiments may be coupled directly to the microfiltration unit 51 and serve the dual purpose of removing filtrate from microfiltration unit 51 and driving feed flow across downstream elements, such as SPTFF 56), a SPTFF 56, a permeate (or filtrate)

pump 58 and a second tank 60 to hold the retentate. A line 62 connects an outlet 64 of the first tank 52 to an inlet 66 of the feed pump 54, and a line 68 connects an outlet 70 of the feed pump 54 with an inlet 72 of the SPTFF 56. A line 74 connects a retentate outlet 76 to the second tank 60, while a line 78 connects a permeate outlet 80 to the inlet of the permeate pump 58. A backpressure control valve 82 may be disposed in the line 74 between the retentate outlet 76 and the second tank 60. The lines 62, 68, 74, and 78 may further include connectors, clamps and other equipment not illustrated in FIG. 1.

As is also illustrated in FIG. 1, a control system 120 is provided. The feed pump 54 and the valve 82 may be set manually, while the permeate pump 58 is controlled by the control system 120 according to the control method illustrated in FIG. 2. According to other embodiments, control system 120 may be coupled to the feed pump 54, the permeate pump 58 and the valve 82, and may be configured or adapted to control the feed pump 54, the permeate pump 58 and the valve 82.

According to certain embodiments, the control system 120 may include one or more processors 122 and memory 124, the memory 124 coupled to the one or more processors 122. The one or more processors 122 may be programmed to control the permeate pump 58, and optionally the feed pump 54 and the valve 82, according to the control method illustrated in FIG. 2. The instructions executed by the one or more processors 122 may be stored on the memory 124, which memory 124 may comprise tangible, non-transitory computer-readable media or storage media, such as read-only memory (ROM) or random access memory (RAM) in a variety of forms (e.g., hard disk, optical/magnetic media, etc.).

The control system and method according to this disclosure utilizes a strategy of variable flow reduction factor (FRF) to achieve a target volume reduction factor (VRF). The FRF is defined as the ratio of the feed flow to retentate flow (feed flow/retentate flow). The VRF is defined as the ratio of cumulative feed volume to cumulative retentate volume (feed volume/retentate volume). To achieve a desired target VRF with a variable flow conversion, the control system and method according to this disclosure implements a permeate flow control strategy with changes in the FRF over the course of the harvest. In particular, a lower target FRF is utilized when the product concentration is high (i.e., at the beginning of the harvest process). By contrast, a higher target FRF is used when the product concentration is low. As the product concentration changes from high to low, the target FRF is varied.

According to a first embodiment of the present disclosure, the target FRF is varied in a series of stepwise changes. The permeate flow control strategy may be expressed as follows:

$$\text{Total VRF} = \Delta T_{total}/(\Delta t_1/\text{FRF}_1 + \ldots \Delta t_n/\text{FRF}_n) \quad \text{(Eqn. 1)}$$

where Total VRF=cumulative volume reduction factor;
$\Delta T_{total}$=total processing time;
$\Delta t$=time interval of a step; and
FRF=volume reduction factor of a step.

Figure 2:
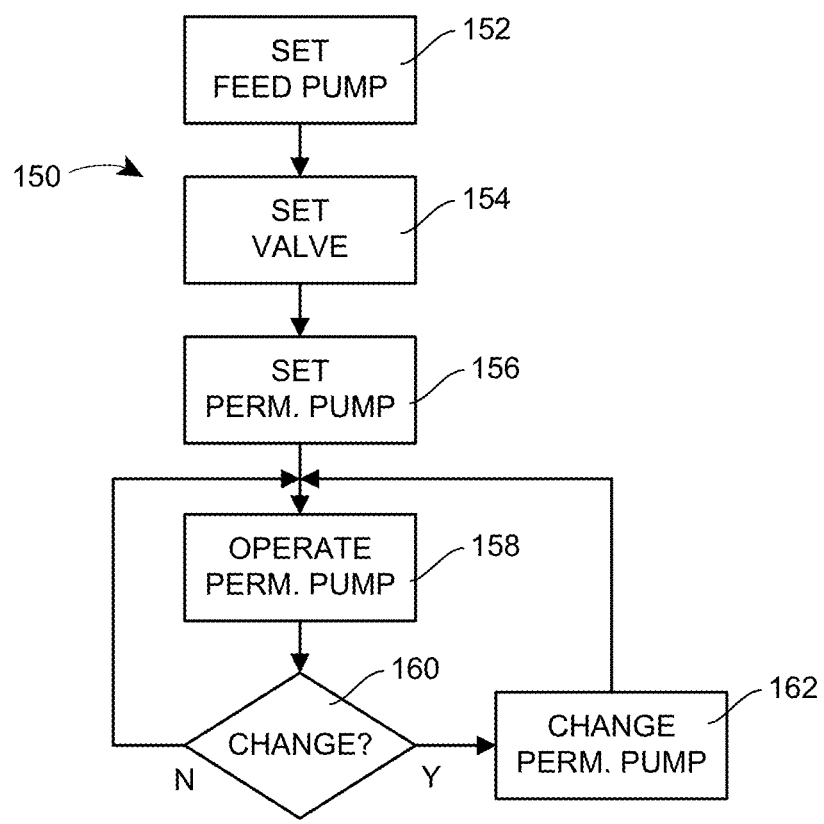
FIG. 2 is a block diagram of a stepped or tiered control method implemented by the control system of FIG. 1.

FIG. 2 illustrates an embodiment of the control method, designated as control method 150. The method 150 begins at block 152, wherein the feed pump 54 is set to run at the required bioreactor perfusion rate. The method 150 continues to block 154, wherein the backpressure control valve 82 is set to the required backpressure for the SPTFF 56. It will be recognized that the actions at blocks 152, 154 may be performed consecutively or simultaneously. The method 150 continues to block 156 wherein the permeate pump 58 is set at a designated pump speed to achieve the target FRF. The method 150 then continues to block 158, wherein the permeate pump 58 is operated at the designated pump speed. The method passes to block 160, wherein a determination is made whether the operation of the permeate pump 58 should be adjusted to vary the target FRF. If the determination is made at block 160 that it is not yet time to change the permeate pump speed to cause the target FRF to change (and with reference to a particular embodiment, to increase), the method 150 returns to block 158. If the determination is made at block 160 that the pump speed should be changed, then the method 150 passes to block 162 where the pump speed is changed to achieve the new target FRF.

Figure 3:
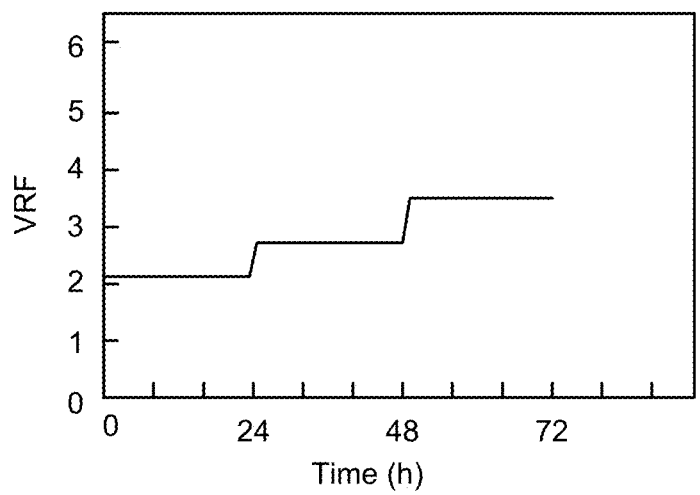
FIG. 3 is a graph of the volume reduction factor (VRF) over time for an example of a stepped control method according to the embodiment of FIG. 2.

FIG. 3 illustrates an example of the FRF achievable through the use of the SPTFF system according to this disclosure in combination with the stepped control system and method. It will be recognized that the method was carried out in three steps over a 72 hour period Each step was performed for a 24 hour period. In keeping with the above-discussion, the FRF used for the first step is low when the product concentration is high, and the FRF used for the third and last step is high when the product concentration is low. In particular, the FRF used for the first step is 2.1, the FRF used for the second step is 2.7, and the FRF used for the third step is 3.4. Using Equation 1, above, the total VRF as a consequence is 2.6.

Figure 4:
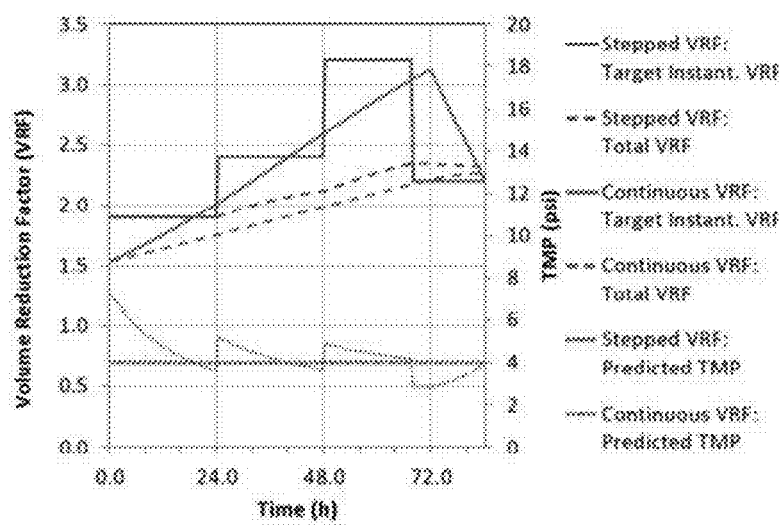
FIG. 4 is a graph of the volume reduction factor (VRF) over time for an example of a stepped control method and a continuously variable control method.

While the example of FIG. 3 includes three steps, it will be recognized that a smaller or greater number of steps may be used (e.g., two steps, four steps). In fact, FIG. 4 illustrates an embodiment of the present disclosure, wherein an embodiment where the FRF is conducted in a step-wise fashion is compared with an embodiment where the FRF is varied continuously. Further, while each step is performed over the same time period, the time period for which a permeate pump speed may be maintained to achieve a target FRF may be varied, such that the first step may be longer than successive steps, or vice versa. Furthermore, while the changes (in this case increases) in target FRF were substantially equal in the example of FIG. 3, it will be recognized that the differential between the target FRFs for successive steps need not be substantially the same.

The target VRF may be achieved by sizing the membrane area according to the feed flow, and specifying a FRF within the pressure constraints of the system Each stepwise change in FRF may be specified to operate within a certain trans-membrane pressure (TMP) window to provide the desired total VRF.

Figure 5:
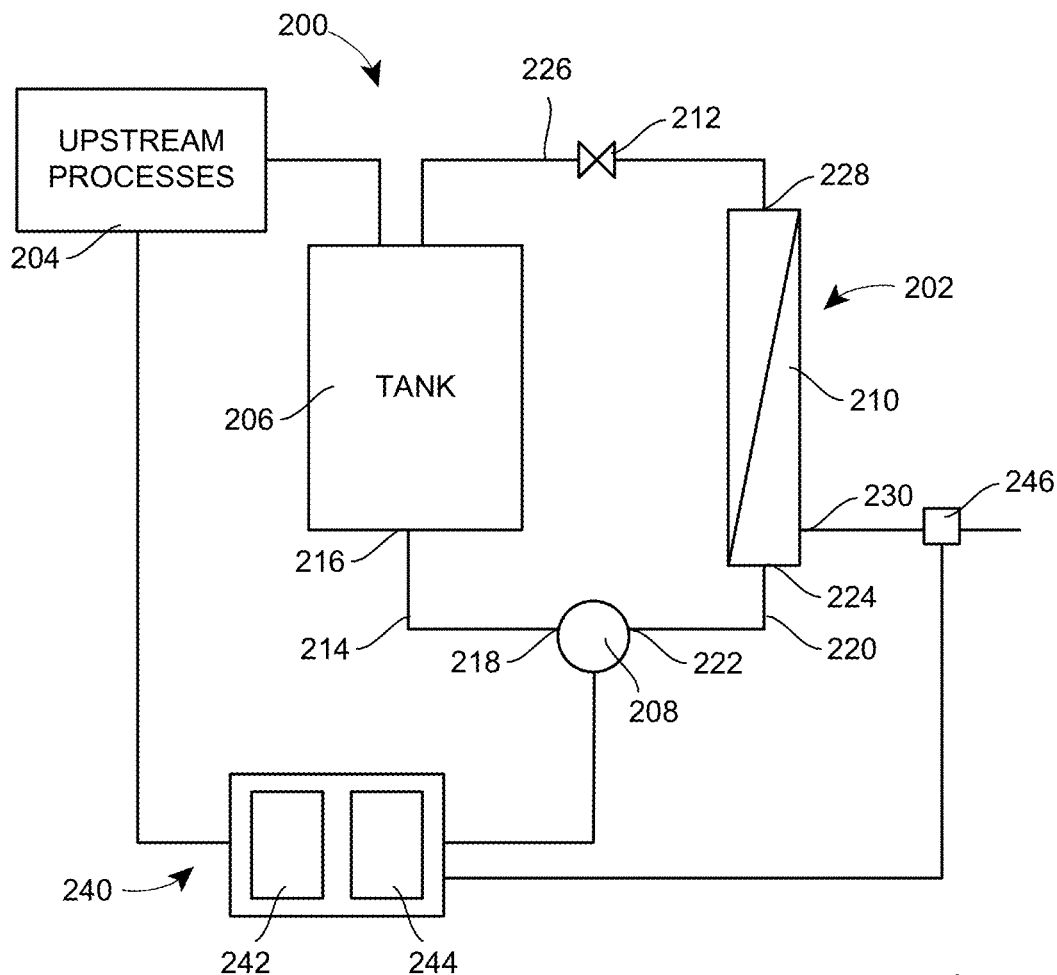
FIG. 5 is a schematic diagram of a control system used in combination with a connected processing system.

Having discussed process control systems and method for concentration of microfiltration harvest fluid, other process control systems and methods used with ultrafiltration and connected processes may be discussed with reference to FIGS. 5-10. In particular, FIG. 5 illustrates a connected-process system (with associated control system) that may carry out the methods of FIGS. 6-10.

As discussed above, ultrafiltration is a separation process that uses a membrane to separate the product of interest, a protein for example, from smaller peptides and salts, for example. In the case of ultrafiltration, the retentate is collected for possible further processing, packaging, etc., while the permeate or filtrate is removed. Ultrafiltration results in a concentrated product, with a lower salt content. Thus, ultrafiltration may also be referred to as a desalting process.

In a typical ultrafiltration process, such as for monoclonal antibodies (mAb) for example, the ultrafiltration process is run as a discrete unit operation in batch mode at a fixed feed crossflow rate. The process is discrete in the sense that the unit is not directly connected to upstream or downstream processes, but instead is operating in batch mode. The fixed feed crossflow rate selected is typically the maximum feed crossflow rate allowable by system design to maximize process efficiency.

As the product concentration increases, the permeate flux decreases. This decrease is commonly attributed to the concentration polarization gradient. That is, as the filtration process proceeds, a boundary layer of substantially high concentration of the substances being retained builds up on or near the surface of the membrane. The boundary layer impedes the flow of material through the membrane, and thus affects the production of the permeate.

In fact, if the ultrafiltration process is operated in batch mode with a feed tank attached to the filter, the inlet flow rate to the filter from the feed tank typically will be decreased to match the permeate flow rate to maintain a constant retentate volume per unit time. Because the ultrafiltration is operated as a discrete unit operation, there is no impact to any other unit operation because of this flow rate decrease.

However, FIG. 5 illustrates a system 200 in which the ultrafiltration processing unit 202 is connected to upstream processing units 204 (e.g., chromatography processing unit, viral filtration processing unit). The ultrafiltration processing unit 202 includes a tank (or recirculation vessel) 206 into which the product of upstream processes is fed, a feed pump 208, a tangential flow filter (TFF) 210, and a backpressure valve 212. A line 214 is connected to an outlet 216 of the feed tank 206 and an inlet 218 of the pump 208. A further line 220 is connected to an outlet 222 of the pump 208 and an inlet 224 of the filter 210. A further retentate return line 226 is connected to an outlet 228 of the filter 210 and the feed tank 206. Permeate exits the ultrafiltration processing unit 202 at the permeate outlet 230 of the filter 210.

Where the ultrafiltration process unit 202 is connected to upstream processes as in FIG. 5, any decrease in permeate flow rate (i.e., at outlet 230) would have an effect on upstream operations. That is, it is typical to decrease the inlet flow rate to the filter to match decreases in permeate flow rate. On the other hand upstream process operations such as chromatography and virus filtration, are typically run at a constant flow rate. If the upstream process operations are to be connected to the ultrafiltration processing unit 202, a solution must be provided to address the differences in operation between the ultrafiltration processing unit 202 and the upstream operations 204. According to the embodiments of this disclosure, a control system is method is required to address the desire to run upstream processes 204 (e.g., the chromatography processing unit) at a constant flow rate and connect those processes (directly or indirectly through a viral filtration processing unit) to an ultrafiltration process unit 202 having a variable permeate flow rate.

As is illustrated in FIG. 5, a control system 240 may be provided. The control system 240 may be coupled to the upstream processes 204 and/or the feed pump 208. The control system 240 may be configured or adapted to control the upstream process 204 and/or the pump 208 to carry out one or more of the control methods described in FIGS. 6-10. The control system 240 may also be coupled to at least one sensor 246 from which the permeate flow rate may be determined.

According to certain embodiments, the control system 240 may include one or more processors 242 and memory 244, the memory 244 coupled to the one or more processors 242. The one or more processors 242 may be programmed to control the upstream processes 204 and the pump 208, according to the control methods illustrated in one or more of FIGS. 6-10. The instructions executed by the one or more processors 242 may be stored on the memory 244, which memory 244 may comprise tangible, non-transitory computer-readable media or storage media, such as read-only memory (ROM) or random access memory (RAM) in a variety of forms (e.g., hard disk, optical/magnetic media, etc.).

Figure 6:
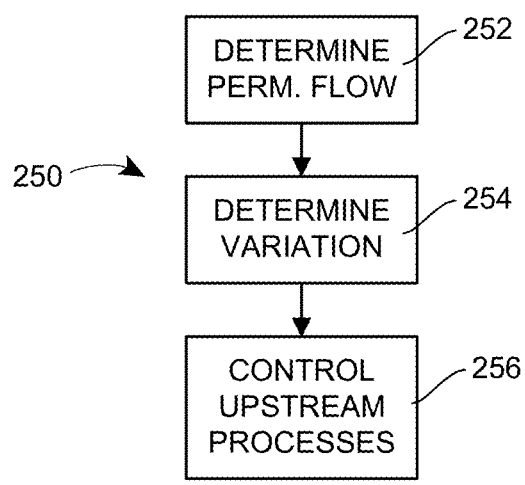
FIG. 6 is a block diagram of a variable flow control method implementable by the control system of FIG. 5.

According to a first method 250, illustrated in FIG. 6 and referred to as a variable flow strategy, the control system 240 varies the operation of the upstream processes 204. In particular, the method 250 begins at block 252, where the control system 240 determines that the permeate flow rate is decreasing, for example in response to a signal received from the sensor 246. The method 250 continues to block 254, where a variation in upstream processes is determined according to the sensed decrease in the permeate flow rate. In other terms, the method 250 determines the appropriate response at block 254 for the sensed change in permeate flow rate. For example, the determined variation may be a predetermined decrease to the flow rate of the upstream processes 204 (e.g., the flow rate of the chromatography processing unit) to maintain a constant retentate volume. According to other embodiments, the variation may be a decrease that is calculated according to a formula that relates the permeate flow rate to the flow rate of upstream processes 204. The method 252 then controls the upstream processes 204 at block 256 according to the variation determined at block 254.

Figure 7:
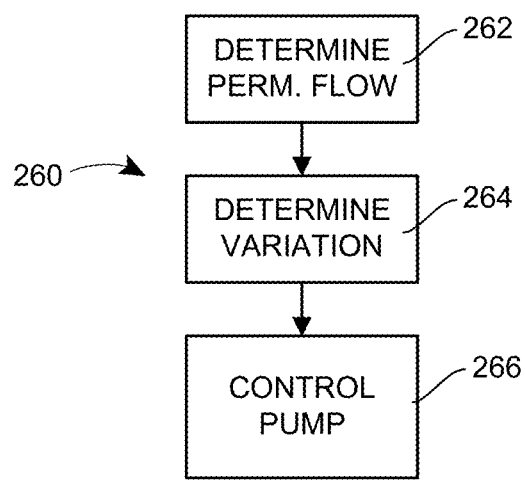
FIG. 7 is a block diagram of a constant flow control method implementable by the control system of FIG. 5.

According to a second method 260, illustrated in FIG. 7 and referred to as a constant flow strategy, the control system 240 varies the operation of the pump 208. In particular, the method 260 begins at a block 262 where the control system 240 determines that the permeate flow rate is decreasing, for example in response to a signal received from the sensor 246. The method 260 continues to block 264 where a variation in the operation of the pump 208 (i.e., an increase or decrease in the flow rate at the outlet of the pump 208) is determined according to the sensed decrease in the permeate flow rate. For example, the variation may be a change in the feed crossflow rate to change the permeate flow rate to a constant flow rate, which rate is matched to the flow rate of the upstream processes 204, which should also provide for a constant volume in tank 206. In this regard, it should be noted that the permeate flux is strongly dependent on the feed crossflow rate; with a higher feed crossflow rate resulting in a higher mass transfer coefficient, thus effecting a higher permeate flux. The method 260 may then continue to block 266 where the control system 240 controls the operation of the pump 208 according to the variation determined at block 264.

A further method for addressing the conflict may also be to allow the flow rates of the upstream processes 204 and the permeate from the outlet 230 to be mismatched. According to this method, also referred to as the variable volume strategy, the tank 206 must be adequately sized to accommodate surges (i.e., increases or decreases) in retentate volume caused by the mismatch. Unlike the methods 250, 260 described in FIGS. 6 and 7, this method is not an active control method, but a passive control method.

Figure 8:
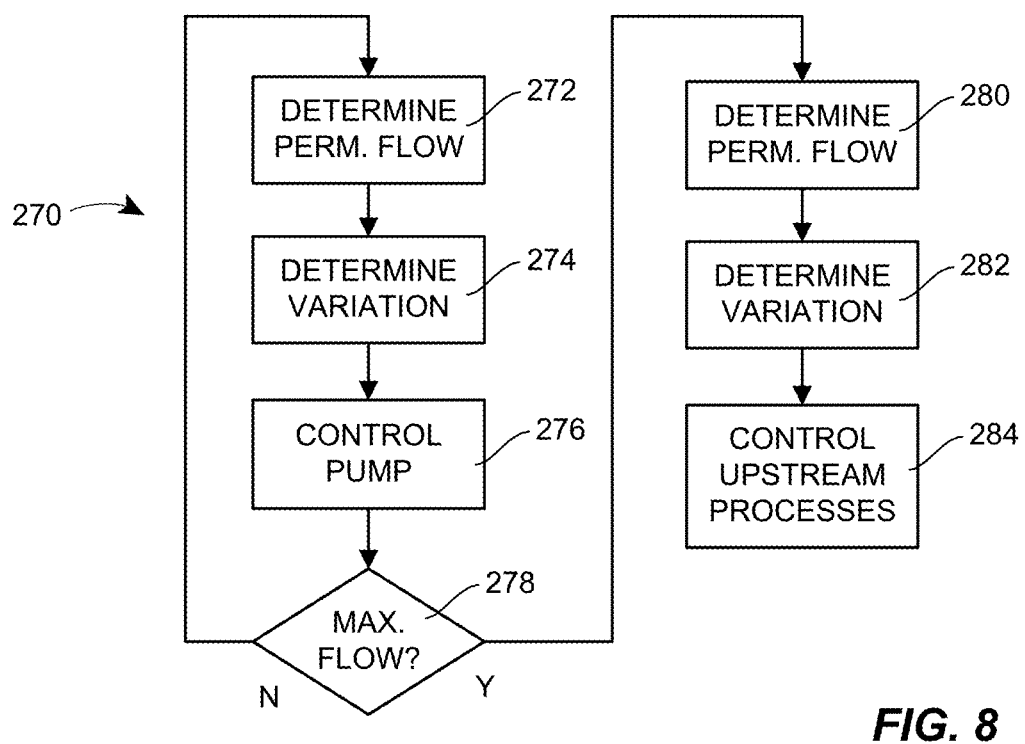
FIG. 8 is a block diagram of a hybrid control method implementable by the control system of FIG. 5.
Figure 9:
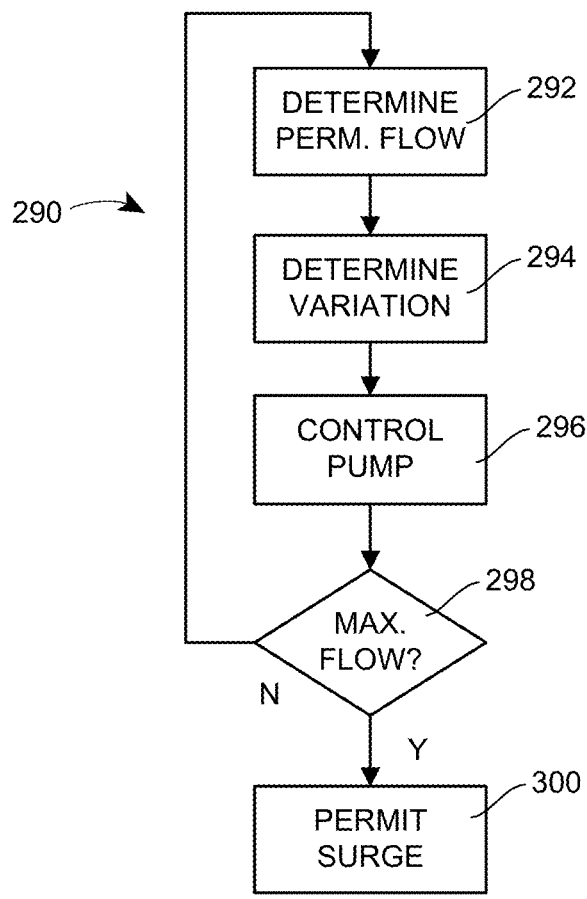
FIG. 9 is a block diagram of a surge control method implementable by the control system of FIG. 5.
Figure 10:
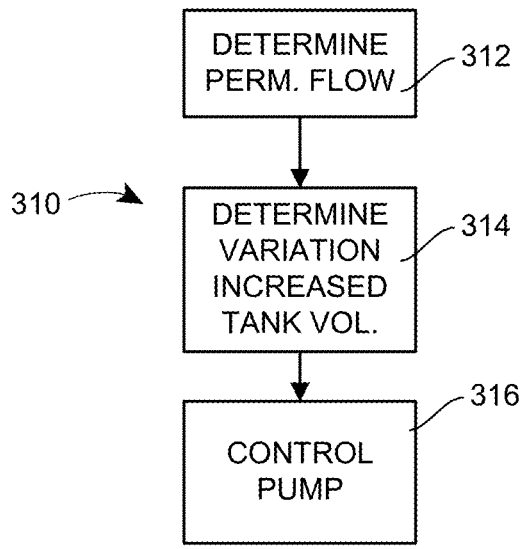
FIG. 10 is a block diagram of a high volume setpoint, fixed flux control method implementable by the control system of FIG. 5.

FIGS. 8-10 illustrate three additional control methods that may be carried out by the control system 240, with the control method of FIG. 8 being referred to as the hybrid strategy, the control method of FIG. 9 being referred to as the surge strategy (which is different than simply permitting a surge to occur in the tank 206), and the control method of FIG. 10 being referred to as the high volume setpoint, fixed flux strategy.

According to method 270 illustrated in FIG. 8, the method 270 uses the steps of the method 260 initially. That is, the method 270 determines if there has been a change in permeate flow rate at block 272, determines a variation for the pump 208 at block 274 and implements the variation at block 276. The method 270 then determines at block 278 if a predetermined flow rate has been reached for the operation of the pump 208, the method 270 proceeds to blocks 280, 282, 284, wherein the method 270 determines if there has been a decrease in the permeate flow rate, determines a variation for the upstream processes 204, and implements the variation. According to certain embodiments, the predetermined flow rate may be the maximum system flow rate. As a consequence of limiting the operation of the pump 208 according to the predetermined flow rate (and in particular, the maximum system flow rate), the variations determined at block 282 and implemented at block 284 are reduced relative to the method 250. Further, a fixed retentate volume is maintained, allowing for smaller tank requirements.

According to the method 290 illustrated in FIG. 9, the method 290 also uses the steps of the method 260 initially. That is, the method 290 determines if there has been a change in permeate flow rate at block 292, determines a variation for the pump 208 at block 294 and implements the variation at block 296. The method 290 then determines at block 298 if a predetermined flow rate has been reached for the operation of the pump 208, the method 270 proceeds to block 300 where the tank volume is allowed to surge according to the passive method described above. According to certain embodiments, the predetermined flow rate may be the maximum system flow rate. The method 290 has the benefit of permitting the upstream processes 204 to continue operating at constant flow rate.

According to the method 310 illustrated in FIG. 10, a larger tank 206 is used to minimize the concentration in the ultrafiltration processing unit 202. As stated above, the product concentration is the primary contributor to polarization gradient formation. By limiting the maximum concentration in the unit 202 relative to a conventional TFF batch ultrafiltration processing unit, the maximum permeate flux rate that can be achieved is increased relative to the convention batch processing unit. The consequence of a higher maximum permeate flux rate is that the upstream processing units may be maintained at the constant flow rate desirable to optimize their performance.

Thus, according to the method 310 illustrated in FIG. 10, the control system 240 varies the operation of the pump 208. In particular, the method 310 begins at a block 312 where the control system 240 determines that the permeate flow rate is decreasing, for example in response to a signal received from the sensor 246. The method 310 continues to block 314 where a variation in the operation of the pump 208 is determined according to the sensed decrease in the permeate flow rate. For example, the variation may be a change in the feed crossflow rate to change the permeate flow rate to a constant flow rate, which rate is matched to the flow rate of the upstream processes 204, which should also provide for a constant volume. However, the variation is also dependent on maintaining a volume in the tank 206 that is larger than the volume maintained by the method 260 in FIG. 8. The method 310 may then continue to block 316 where the control system 240 controls the operation of the pump 208 according to the variation determined at block 314.

It will be further recognized that the upstream processing units 204 may not provide a sufficient mass for each cycle of the processing units 204 for the methods illustrated in FIGS. 6-10 to be used continuously throughout the operation of the connected system 200. Instead, the variable volume strategy described above may be used to cause the volume in the tank 206 to surge, thereby collecting and combining multiple connected cycles from the upstream processing units 204.

As will be recognized, the systems and methods according to this disclosure may have one or more advantages relative to conventional technology, as has been explained above. Any one or more of these advantages may be present in a particular embodiment in accordance with the features of this disclosure included in that embodiment. Other advantages not specifically described herein may also be present as well.

Experimental Testing

Figure 11:
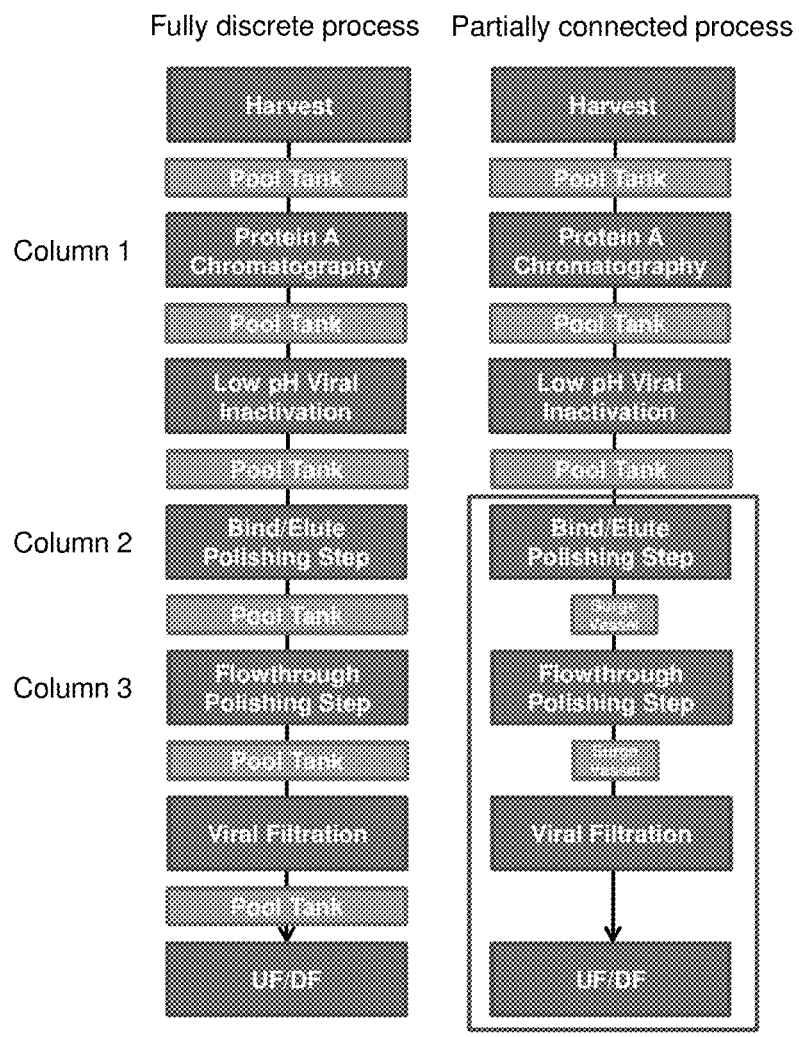
FIG. 11 illustrates a three-column mAb purification process with column 2 and 3 as polishing steps, wherein column 2 is typically cation exchange chromatography operated in bind and elute mode and column 3 is commonly specified as anion exchange chromatography operated in flowthrough mode, and wherein the box indicates the steps that are operated concurrently in a connected process, and large pool tanks can be converted to small surge vessels in a connected process.

By way of example, various advantages and benefits have been realized through the following experimental activities. Specifically, the following description presents one experimental mAb downstream process that is connected from the polishing columns through the final tangential flow filtration (TFF) step. A typical mAb platform process is described in FIG. 11, which begins with harvest and is followed by protein A affinity chromatography for capture, a low pH viral inactivation step, up to two additional chromatography steps for polishing, a viral filtration (VF) step, and finally a TFF step to perform ultrafiltration/diafiltration (UF/DF) for formulation. The intermediate pools between the polishing columns, in this case a bind/elute (B/E) and a flowthrough (FT) step, and TFF are usually the most dilute pools, and therefore have the highest potential for their volumes to exceed the size of the pool tanks. By connecting the B/E column, FT column, VF, and TFF steps, three large pool tanks can be reduced or eliminated. This paper reports proposed configurations of the connected process and flow control strategies to enable the connectivity of the unit operations. A detailed description is provided on how to approach the development of a connected process, as well as considerations for additional process monitoring requirements.

Methods and Materials

Materials

Five mAb products (mAb A, mAb B, mAb C, mAb D, mAb E) were produced with standard CHO cell culture methods.

Chromatography resins used at small and large scale include Fractogel® EMD $SO_3^-$ (EMD Millipore, Billerica, Mass.) and Phenyl Sepharose™ 6 Fast Flow High Sub (GE Healthcare, Piscataway, N.J.). Small-scale chromatography columns were packed in 1.15 cm EMD Millipore Vantage™ L laboratory columns, and at large-scale in GE Healthcare Axichrom 60 or 80 cm columns. AEX membranes Sartobind STIC® (Sartorius Stedim, Goettingen, Germany) were used in either the Nano (1 mL) or 10" (180 mL) sizes. Viresolve® Prefilter (5 cm², 0.55 m² and 1.1 m²), Viresolve Shield (3.1 cm² and 0.51 m²), Viresolve Pro (3.1 cm² and 0.51 m²), and Pellicon® 3 Ultracel® 30 kDa (0.0088 m² and 1.14 m²) filters were purchased from EMD Millipore.

Small-scale chromatography and connected process experiments were performed on GE Healthcare AKTAexplorer™ 100 systems. For connected process experiments, multiple AKTAs were connected to each other via the remote connections on the back of the P-900 pumps to allow auxiliary input and output signals to be passed between instruments. Pressure monitoring of the small-scale prefilters and virus filters was performed with SciPres® (SciLog, Madison, Wis.) pressure sensors and pressure monitor. An EMD Millipore Amicon® stirred cell (50 mL) was used as a surge vessel; the vessel was used without the top cap and membrane, so it could operate open to atmospheric pressure as a continuously stirred cell placed on a magnetic stir plate.

Small-scale discrete viral filtration experiments were performed with a constant pressure setup, which includes a pressure regulator, pressure vessel (300 or 600 mL polycarbonate), pressure gauges, a balance serially connected to a computer for data collection, and a compressed air supply. Small-scale TFF experiments were performed on an AKTAcrossflow™ system.

Large-scale runs were performed on custom-built automated chromatography, viral filtration and TFF skids. The chromatography skids included tertiary pumps for gradient and dilution capability, inline monitoring of pressure, flow, pH, conductivity, and UV. The skids were also equipped with a split stream valve and pump to collect pseudo-pool samples of product pools. The viral filtration skid included holders for the pre-filter and virus filter, and inline monitoring of pressure, flow, pH, conductivity, UV. The TFF skid included a 200 L retentate tank, diaphragm pump for the system feed and peristaltic pump for the diafiltration buffer, automated TMP control valve, inline monitoring of pressure, flow, pH, conductivity, and level sensing on the retentate tank. Surge tanks were equipped with level sensing.

Methods

Sartobind STIC Membrane Chromatography

Sartobind STIC experiments were performed on an AKTAexplorer with the mixer bypassed. An in-line filter (0.2 μm Sartorius Minisart) was used upstream of the STIC membrane to prevent pressure build-up by filtering away particles potentially generated by the AKTA pump. Load material was either filtered, low pH viral inactivated pool (FVIP) or CEX pool. Product pools were collected either as a single main fraction or in multiple fractions during flow through and wash. Assays performed on the STIC pool include CHOp ELISA (for CHO host cell protein), DNA QPCR and concentration UV A280.

Inline pH Titration

CEX elution fractions were created by an AKTAexplorer which ran the entire CEX operation sequence through an automated program Each fraction was then used to screen pH titrants manually. After an appropriate titrant was found, an experiment employing two AKTAexplorers was executed to confirm that the chosen titrant could provide accurate inline pH titration to the target. The first AKTA ran CEX and its elution was collected into a beaker as the surge vessel with 5-minute residence time. The second AKTA loaded product from the beaker with pump A and titrant with pump B. The two streams were mixed in the mixer and then measured for pH by the inline pH probe on the second AKTA. The second AKTA also performed fractionation and the pH of each fraction was verified using an Orion Dual Star offline pH meter (Thermo Scientific, Waltham, Mass.).

Viral Filtration

Viral filter testing was performed either in discrete or connected mode, with the pre-filter and viral filter placed in series. Discrete testing was performed using the constant pressure setup described in the materials section, collecting volume filtered over time with a homogenous feed loaded onto the filters. Connected testing was performed using the connected AKTAexplorer setup, with the pre-filter and viral filter on one AKTA connected to the preceding chromatography step(s) on separate AKTAs and a surge vessel in between each step. The surge vessel was operated at a fixed residence time and therefore volume, typically 5-7 minutes. Unicorn methods were programmed to enable automated signaling between AKTAs to start and end the loadings and elutions. Inline titration, conditioning, or dilutions were performed with the AKTA B-pump, mixed with the feed stream loaded on the AKTA A-pump. Since the small-scale setup uses fixed column diameters and filter areas based on commercial availability, in order to achieve the targeted loadings and flow rates on the intermediate connected unit operations comparable to large-scale operations, a split stream was taken with the AKTA sample pump after the chromatography step and before the surge vessel. This split stream enables control of the flow rate for the subsequent unit operation, and since mass and flow rate are linked in connected process, the mass loading is also controlled. Material collected from the split stream was used to generate a pseudo-product pool for assessing the yield and impurity removal performance of the each connected step.

TFF Flux Excursions

Flux excursion experiments were performed on an AKTAcrossflow by obtaining permeate flux measurements at a range of protein concentration (typically 10-80 g/L), feed cross flow (1-6 L/min/m² or LMM), and TMP (10-25 psi) to empirically determine the stagnant film model parameters (see equations below). Flux excursions were performed using protein in the salt buffer from the prior unit operation to best model the performance during the connected UF phase (UF1a). Product was allowed to recirculate at each concentration, TMP, and feed crossflow until stable permeate flux and Delta Pressure (Feed—Retentate) was achieved. Data points where the permeate pressure was greater than 4 psi were excluded from the analysis. After each set of TMP measurements, the membrane was depolarized by recirculation with the permeate outlet closed. This data was then plotted in terms of flux (J) versus the natural log of $C_b$ (protein concentration of the test).

Filter Sizing

Viral filter area sizing depends on the connected process flow rate and the maximum allowable operating pressure. The lowest observed viral filter permeability (filter flux normalized for pressure drop) occurs at the peak of the protein concentration. This lowest observed permeability ($k_{VF,min}$) can be used to set a maximum flux ($J_{VF,min}$) that can be operated within the maximum pressure limit ($P_{VF,min}$), as described by $J_{VF,max} = k_{VF,min} \times P_{VF,max}$. The required filter area ($A_{VF}$) can be determined by Equation 1, where $Q_{VF}$ is the process flow rate.

$$A_{VF} = \frac{Q_{VF}}{k_{VF,min} \cdot P_{VF,max}} \quad \text{Equation 1}$$

For TFF modeling, the work of Ng P, Lundblad J, Mitra G. 1976. Optimization of solute separation by diafiltration. Separation Science 11(5):499-502 describes the TFF permeate flux based on the stagnant film model. The stagnant film model can be modified to include a feed cross flow dependence in the mass transfer coefficient ($k = k_o v^n$), where $k_o$ is an empirical constant, $v$ is the feed cross flow, and $n$ is the power term for the feed cross flow dependence. This modified stagnant film model is shown in Equation 2, where $J_{TFF}$ is the permeate flux, $C_w$ is the concentration of protein near the membrane wall, and $C_b$ is the bulk protein concentration.

$$J_{TFF} = k_o v^n \ln \frac{C_w}{C_b} \quad \text{Equation 2}$$

The parameters derived from the flux excursions, combined with input parameters from the process are used to determine the optimal final concentration to target at the end of the connected portion of processing (end of UF1a) by solving Equation 2 for $C_b$. The desired permeate flux is determined from the inlet process flow rate and the TFF filter area. The feed cross flow rate is set at the upper capability of the system and membrane, typically 6 LMM. Equation 3 can then be used to determine the target retentate tank level set point based on the total expected mass for the process, m.

$$V_{end,UF1a} = \frac{m}{C_{b,end\ UF1a}} \qquad \text{Equation 3}$$

Results

Design and Flow Control of a Connected Process

Figure 12:
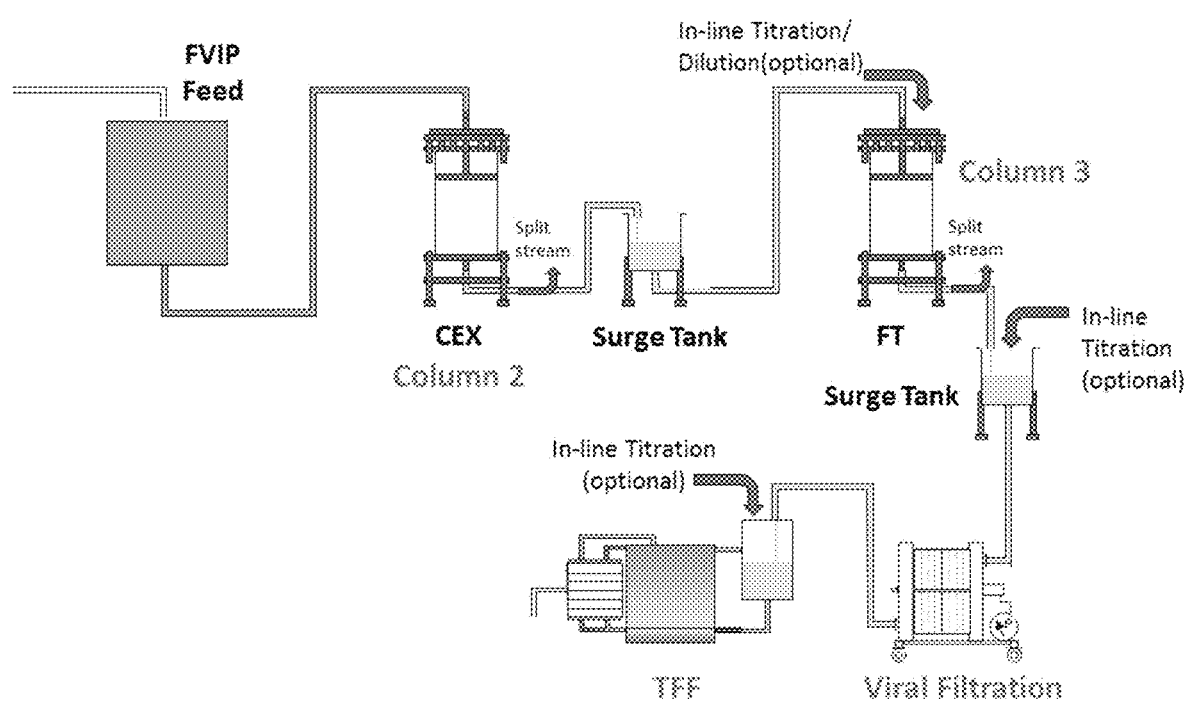
FIG. 12 is a schematic illustration of a connected process design illustrating sequence of operations, connectivity of steps, location of surge vessels, split stream sampling, and inline titrations.

The high-level design of a connected system is similar to a discrete system, in that the main components and functionality of the standard unit operations remains largely the same. In a connected system, large pool vessels are replaced by small surge tanks with short residence times (typically 5-7 minutes), which act as a pressure break between unit operations (FIG. 12). Batch dilutions and titrations are replaced by inline additions. The key to designing the process control of a connected system is determining how to manage flow disparities between unit operations. In the final TFF step, the product is initially concentrated to a desired endpoint for performing diafiltration. The challenge comes in managing the decrease in permeate flux that comes with the increase in product concentration as mass is added to the retentate tank; this decrease in permeate flux is attributed to the effects of concentration polarization on the membrane. For a discrete fed-batch TFF, the inlet flow rate to the retentate tank would decrease to match the permeate flow rate to maintain a constant retentate volume. Since the TFF step is operated as a discrete unit operation, there is no impact to any other unit operation due to this flow rate decrease. However, in a connected process, the inlet stream is directly connected to the previous upstream operation and any decrease in permeate flow rate would cause a flow disparity. For a process sequence that connects a constant flow rate chromatography step with a variable permeate flux TFF step, whether directly or through a viral filtration step, the mismatched flows need to be actively managed. This can be accomplished during the TFF operation using three distinct strategies: 1) a Variable Flow Strategy, 2) a Constant Flow Strategy, or 3) a Surge Strategy (FIG. 13, Table 1). It should be noted that the initial concentration is the only phase that is connected in the final TFF step, because once the product mass is fully contained in the retentate tank, the remainder of the diafiltration and final concentration steps can proceed as a standard discrete process.

In the Variable Flow Strategy, the TFF is operated similarly to a discrete fed-batch operation in that the permeate flux declines as mass accumulates in the retentate tank. To balance the system flow, the flow rates of the upstream unit operations also decrease to match the permeate flux. This maintains a constant retentate volume, but results in a variable flow on the chromatography steps. The magnitude of the flow variation could result in at least a two-fold decrease, which could have potential impact on the performance of the chromatography step.

An alternative is the Constant Flow Strategy, in which both the permeate and inlet flows are maintained at a constant value in order to maintain both a constant retentate volume and a constant flow through the preceding unit operations. To achieve constant permeate and inlet flows, a novel strategy was developed using both TFF feed crossflow rate and transmembrane pressure (TMP) to actively control the permeate flux. The TFF feed crossflow rate is able to directly influence the mass transfer rate and thus the flux through the membrane. The transmembrane pressure (TMP) also controls the permeate flux, although this parameter has diminishing control at higher protein concentrations and higher TMP when the flux-limited regime is reached. In this control strategy, a lower crossflow rate and TMP are used at the outset of the connected process when the product concentration in the tank is low, with a gradual increase in both parameters as the product concentration increases to maintain a constant permeate flow rate. This methodology was developed into an automated control system that simultaneously modulates both input parameters of feed crossflow rate and TMP to achieve a constant permeate outlet flow, and thus enables a connected process system to operate without flow disparities.

The final control strategy, the Surge Strategy, can almost be described as an absence of active flow control. In this strategy, when the permeate flux exhibits a decline, the inlet flow is still maintained at a constant rate, which then induces a volume surge in the retentate tank. In practice, the TFF system would exhibit some self-modulation, in that as the volume surged in the tank, the rate of increase in product concentration would slow, as would the decline in flux.

These three described control strategies represent the available choices for flow control, but ultimately, a blend of these strategies can be used to achieve a global process optimum that balances the requirements for membrane area and processing time, flowrate turndown impacting the previous unit operations, and volume of the retentate vessel. The following sections describe the development of a connected process using the Constant Flow Strategy, with emphasis on the aspects and parameters that are unique to a connected process. This strategy was chosen for its simplicity in operation and process development, since it maintains a constant flow on the chromatography and viral filtration steps and minimizes the number of dynamic effects that need to be studied.

Development of a Connected Process

Development of a process connecting two polishing columns, viral filtration and TFF requires additional considerations as compared to developing these unit operations individually. Such considerations include: 1) evaluating the impact of the B/E column elution on the subsequent steps; 2) developing an inline pH titration method when the subsequent steps need to be operated at a different pH than that of the B/E pool; 3) developing a flow driven viral filtration step with variable feed composition; 4) developing a TFF step with constant permeate flux during the connected process.

Development of the First Chromatography Step

Since the first step in the connected process train is presented with a homogenous load, the filtered viral inactivated protein A product pool, it can be developed independently as a discrete process, and therefore will not be discussed in detail here. However, there are two important considerations for a connected process. First, when a B/E step (e.g. CEX) with gradient elution serves as the first step of the connected process, all subsequent steps experience a product concentration peak and a salt concentration gradient generated by the first step elution. Depending on the maximum product concentration achieved, such a concentration peak could pose challenges downstream, especially for the viral filtration step. To alleviate the impact of a high peak concentration on subsequent steps, a shallower salt elution gradient can be adopted. This would decrease the peak concentration and allow the product to pass through the remaining steps with acceptable back pressure. Second, since all steps are connected, the first step elution volumetric flow rate needs to be optimized based on the capability of the remaining steps.

Development of the Second Chromatography Step

Figure 14A:
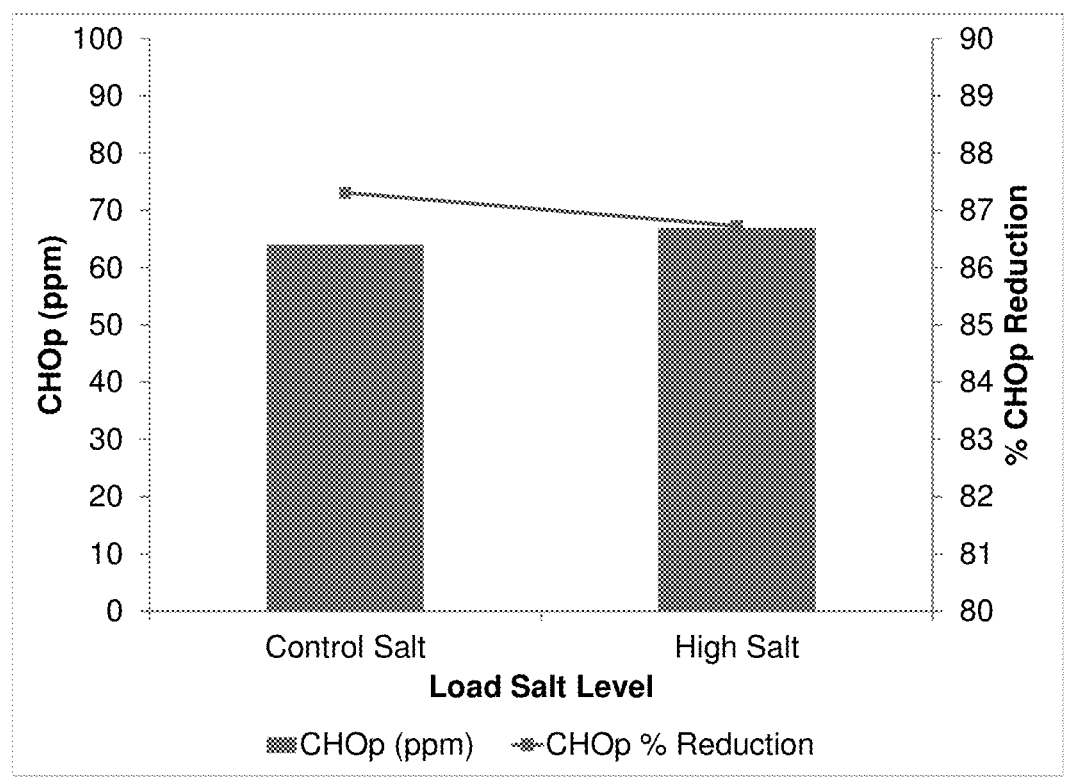
FIG. 14a is a graph of data illustrating the effect of load conductivity on CHOp removal over STIC membrane chromatography (mAb A), wherein control salt and high salt experiments have a load conductivity of 16 and 28 mS/cm, respectively, showing minimal effect of load conductivity on CHOp level in the pool (vertical bars) and % CHOp reduction (angled line)

The second step specified in the connected process schematic is operated in flowthrough mode, and could be either resin-based or membrane-based chromatography. This second step is usually the third and last chromatography step for the entire downstream process, however, it may not be required when a two-column process demonstrates sufficient impurity and virus removal capacity. The purpose of this step for a typical mAb purification process is to remove host cell proteins and potentially further reduce high molecule weight (HMW) and DNA. When this flowthrough step is connected to a B/E step as the first step, its feed is no longer homogenous as operated in discrete mode, but dynamic in terms of protein concentration and conductivity. Conductivity in the flowthrough step feed stream increases during loading, because of the preceding salt gradient elution, and reaches a maximum at the end of loading. Because of this, it is important to select a resin or adsorptive membrane that maintains robust impurity clearance over a wide range of conductivity; the AEX membrane STIC chromatography is one example of a salt-tolerant adsorptive matrix. To evaluate the effect of load conductivity on host cell protein removal, a few discrete flowthrough experiments with variation in load conductivity are sufficient to assess the effect. FIG. 14*a* compares the load conductivity effect on CHOp removal over a flowthrough STIC step. The results show that conductivity does not play a significant role in terms of CHOp removal, as expected based on the high salt tolerance of the ligand optimized for this device. Therefore, elution from the first step can be directly fed into the second connected step without dilution.

Figure 14B:
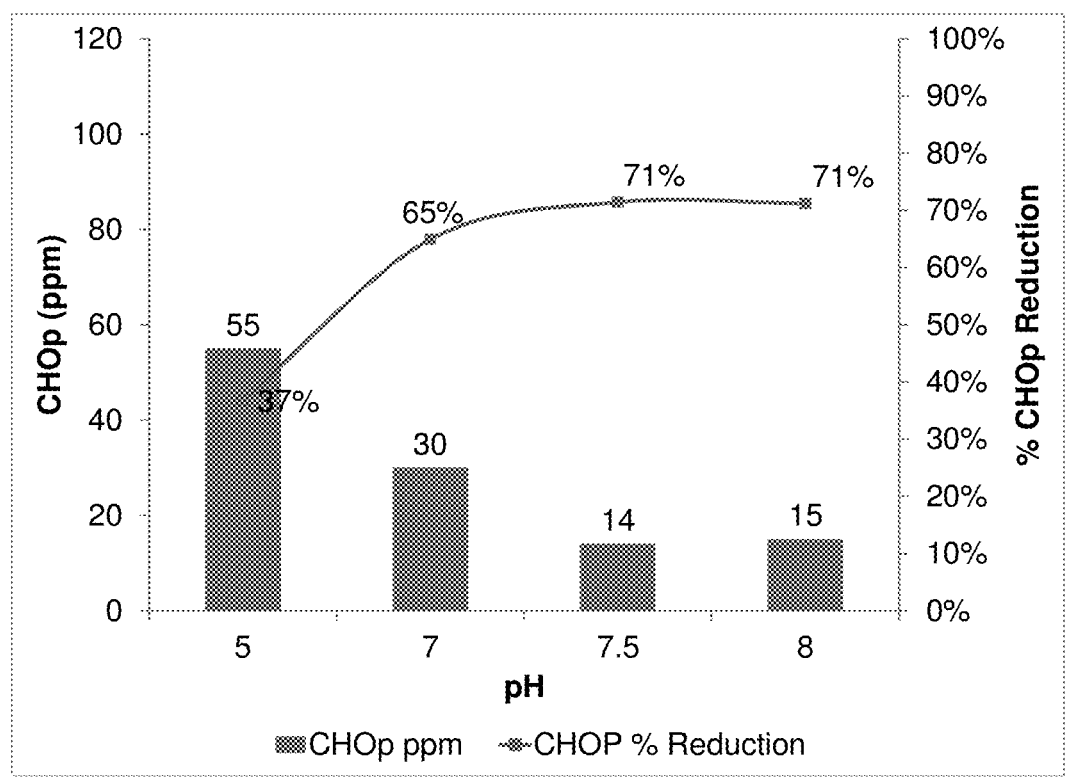
FIG. 14b is a graph of data illustrating the effect of pH on CHOp reduction over STIC membrane chromatography of mAb A, wherein the load material for these four experiments were prepared by titration of a CEX pool (pH 5.0, conductivity 16 mS/cm) with 2 M Tris to their corresponding pH, showing results for CHOp level in the pool (vertical bars) and % CHOp reduction (curved line) show that better host cell protein removal is achieved at higher pH on the STIC.

In order to more effectively remove host cell proteins, the flowthrough step may need to operate at a higher pH than that of the B/E step, such as for an AEX FT step. A few discrete pH scouting experiments are needed to find the optimal operating pH for this flowthrough step. FIG. 14*b* shows that host cell protein removal via AEX membrane chromatography at higher pH provides better clearance. For this example, since all four tested pH values provided acceptable clearance, pH 5 was selected for STIC operation due to the benefits of avoiding a titration step during connected processing. However, for cases in which pH titration is required to achieve desired host cell protein removal, an inline pH titration method is required.

Development of an Inline pH Titration Step pH titration of the intermediate product pool is required when the preceding step uses a different operational pH than the subsequent step. In discrete mode, pH titration can readily be performed by adding a specified amount of titrant into the homogenous product pool to achieve the target pH. However, in the case of a connected process, inline pH titration is required to change the pH of the product stream coming from the previous step, since the product is continuously loaded onto the next step. Product streams that potentially require pH titration in the connected process are the feed streams for flowthrough and viral filtration and occasionally the load for the UF step. Inline pH titration of feed streams for flowthrough and viral filtration steps can be accommodated without an additional pump if the skid or system used for each step minimally has a dual-pump design to deliver feed and titrant streams simultaneously, with subsequent mixing via a passive mixer. An additional pump may be required to deliver titrant into the TFF retentate tank when the UF load requires titration.

Regardless of the location that inline pH titration is introduced, variations in protein concentration and conductivity in the eluate from the bind and elute step need to be considered when selecting a titrant. Furthermore, the process and system design is simplified when titrant is introduced into the product stream at a constant titrant to product volume ratio. This volume ratio should be low to avoid over-dilution of the product stream, but also sufficiently high to be within the pump flow rate linear range. Based on this, a volume or flow ratio of 0.1-0.2 is typically recommended.

Figure 15:
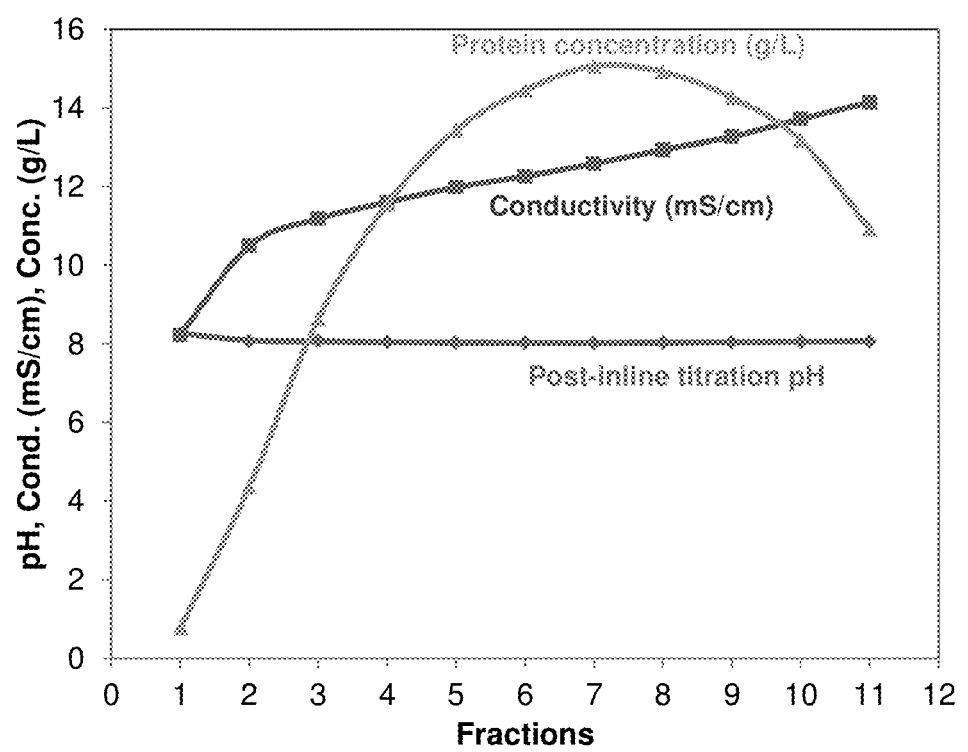
FIG. 15 is a graph of data illustrating inline pH titration of mAb A CEX elution stream from pH 5.0 to pH 8.0 with a titrant of 400 mM Tris pH 8.3 at volume ratio of 0.1, showing results that the target pH (straight horizontal line) was achieved throughout the elution peak (protein concentration, bell curve; conductivity, angled line)

Inline pH titration development starts with offline pH titration of multiple fractions across the elution of the bind and elute step. The product concentration and pH of the titrated fractions are screened to ensure that each fraction reaches the target pH with addition of the titrant at the same volume ratio. After the titrant is identified, a bench scale connected run is employed to verify the results. FIG. 15 shows an inline pH titration from pH 5.0 to pH 8.0 of a CEX elution with a titrant of 400 mM Tris pH 8.3 at volume ratio of 0.1. After inline titration, the product stream was fractionated, and each fraction was analyzed using an offline pH probe. The target pH was achieved throughout the elution peak, as shown in FIG. 15.

Development of the Viral Filtration Step

The initial development of a connected viral filtration step is similar to the development of a discrete step in that molecule and solution properties drive the selection of the appropriate viral filter and prefilter and dictate the hydraulic permeability performance of the membranes. Since the viral filter is connected to preceding unit operations which dictate the flow rate through the filter, it is advantageous to choose a viral filter with high membrane permeability to reduce the membrane area required. Additionally, the viral filter must be able to operate effectively when exposed to variable pressure and a feed composition that varies in both product concentration and conductivity over time. Here, the Viresolve Pro (VPro) filter is used as an example. This filter has a high membrane permeability and generally demonstrates robust operation regardless of molecule, feed composition, and pressure variations, particularly with the use of a prefilter. Commonly used prefilters include depth filter and charge-based prefilters (Ng P, Lundblad J, Mitra G. 1976. Optimization of solute separation by diafiltration. Separation Science 11(5):499-502; Brown A, Bechtel C, Bill J, Liu H, Liu J, McDonald D, Pai S, Radhamohan A, Renslow R, Thayer B, Yohe S, Dowd C. 2010. Increasing parvovirus filter throughput of monoclonal antibodies using ion exchange membrane adsorptive pre-filtration. Biotechnol and Bioeng 106(4):627-637).

Figure 16:
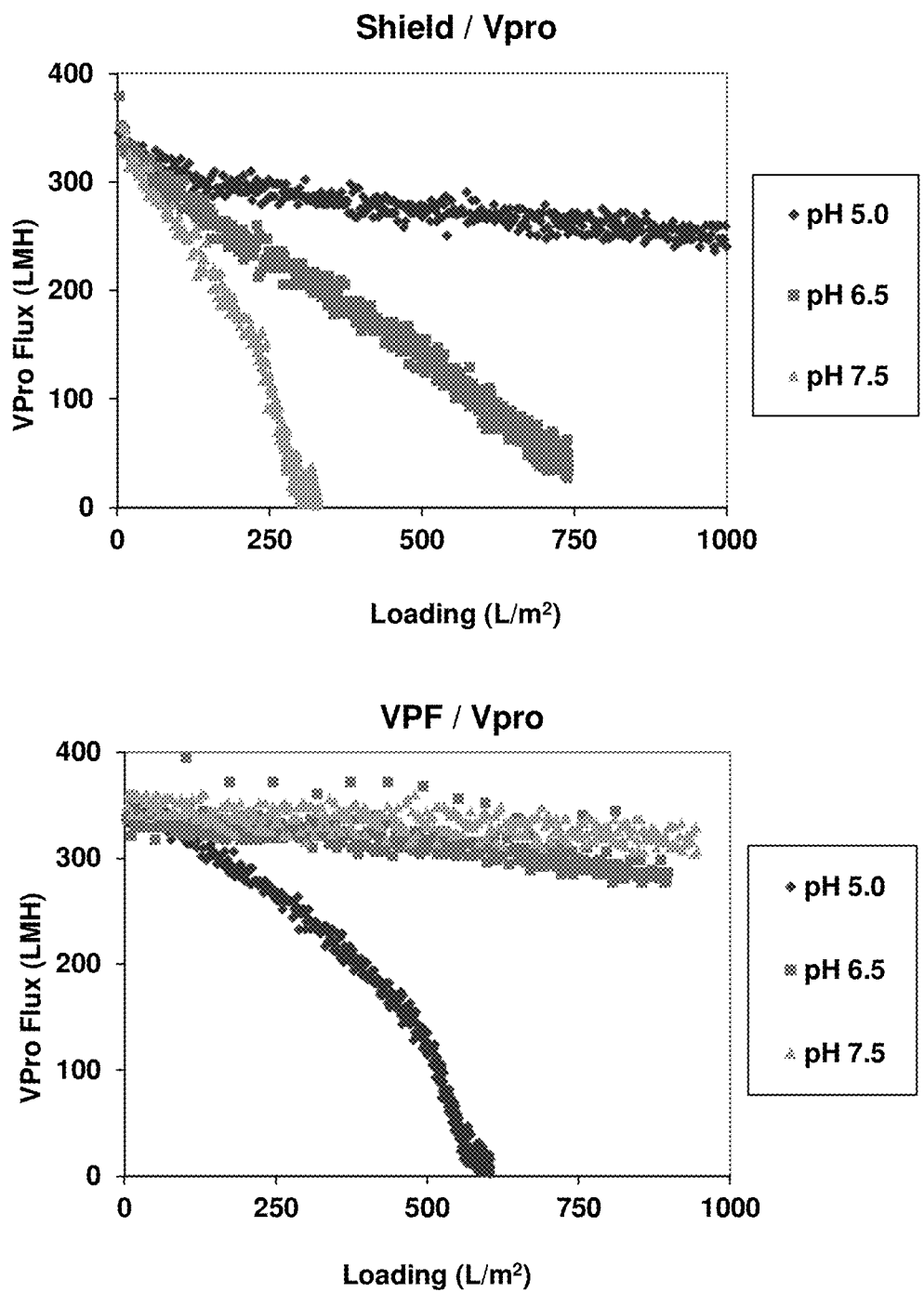
FIG. 16 presents two graphs of data (Top panel: Viresolve Shield; bottom panel: Viresolve Prefilter) evaluating the effect of load pH in batch mode using two different prefilters for the Viresolve Pro with mAb D, wherein test conditions were at 25 g/L protein concentration, 0.1M NaAcetate 0.15M NaCl, 30 psi constant pressure, and wherein conditions are depicted: pH 5.0 (diamonds), pH 6.5 (squares), pH 7.5 (triangles)

Batch filtration experiments using a homogenous feed can provide relative performance comparisons between prefilters with different adsorptive properties. Additionally, batch experiments can be used for screening the optimal pH setpoint of the viral filter load. FIG. 16 shows the effect of pH on the VPro flux when two different prefilters are used: 1) the Viresolve Prefilter (VPF), consisting of diatomaceous earth with charged binders, and 2) the Viresolve Shield, consisting of a negatively-charged membrane. For mAb D, the negatively-charged Shield prefilter shows better performance at low pH, as expected based on the high pI of the mAb, or more specifically the mAb aggregate impurities, and cation exchange mechanism of interaction. Conversely, the VPF prefilter shows better performance at high pH. This could indicate more hydrophobic interaction mechanism at a pH closer to the pI of the molecule and in the high salt solution conditions. This example illustrates the benefit of performing batch studies to assess relative performance of prefilters and pH conditions.

Figures 17A, 17B:
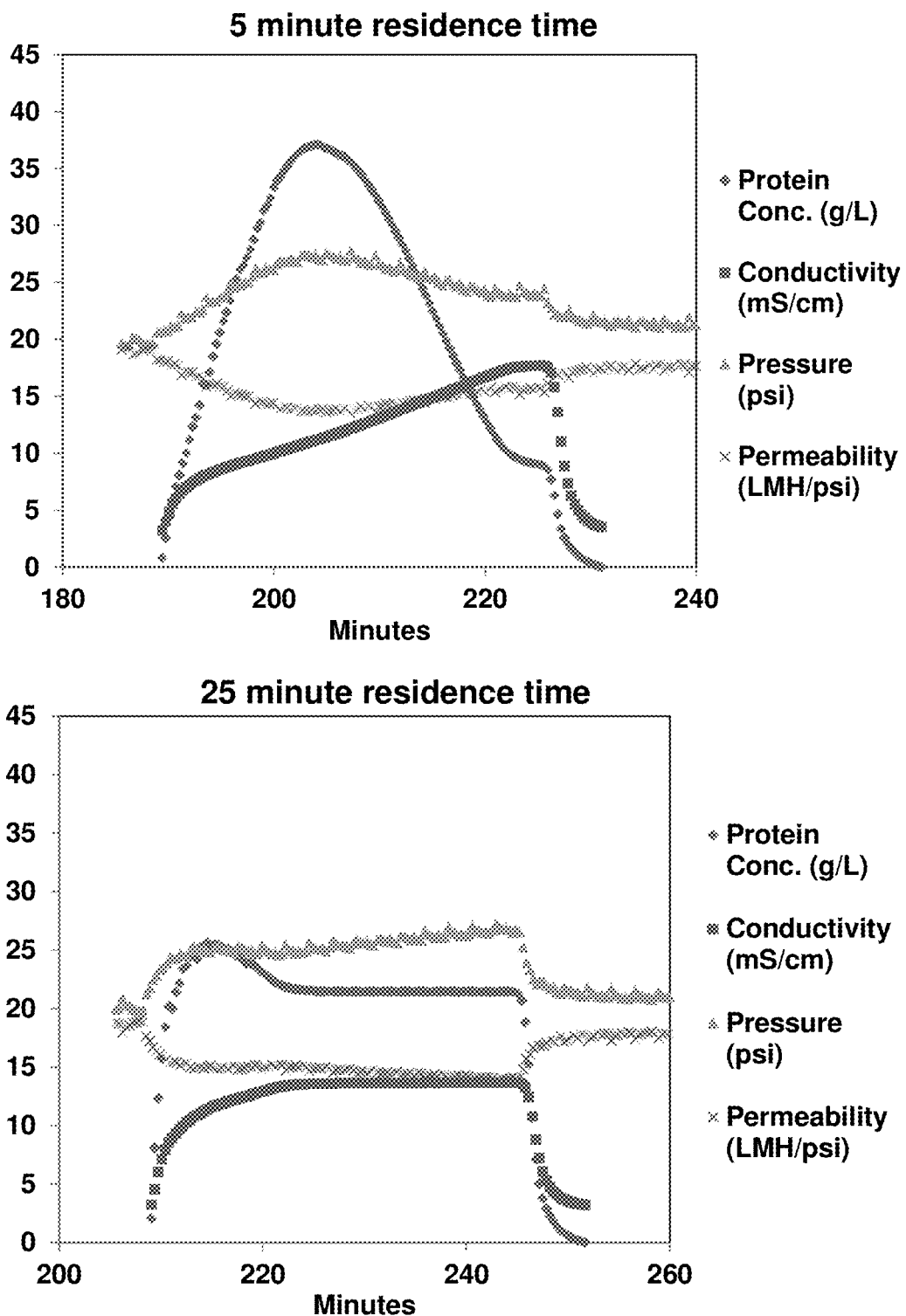
FIGS. 17a and 17b are graphs showing viral filtration profiles for a connected CEX-VF(VPF-VPro) operation with mAb C (in 0.1M NaAcetate pH 5) with a residence time in the intermediate surge vessel of: 17a) 5 min and 17b) 25 min, wherein trends shown for protein concentration (diamonds), conductivity (squares), pressure (triangles), permeability (Xs)

To assess the performance of the viral filter for a connected process, two different approaches can be considered. As in the previous example, experiments can be conducted in batch mode on the viral filter alone; this can be accomplished by creating multiple feed materials with varying product and salt concentrations. These experiments can be conducted as a design of experiment (DoE) to study the relative effects of protein concentration, salt concentration, and even pressure or flow on membrane performance. Ranges can be chosen to evaluate the extremes in product and salt concentration observed from the preceding chromatography step, and to bracket the range of pressures experienced by the viral filter. A second approach for evaluating connected performance is to simulate the actual connected process with a scaled-down system. Such an approach would produce a representative time-variable feed of changing protein and salt concentration from the preceding chromatography step that would be directly loaded onto the viral filter. An example of a connected run with a CEX gradient elution connected to the VPro with a prefilter is shown in FIG. 17a. The variation in protein concentration and conductivity on the viral filter is the result of the elution from the CEX gradient, with a plateau at the end of loading due to the draining of the surge vessel. Since the run is operated at constant flow, the increase in protein concentration leads to an increase in pressure on the viral filter, which corresponds to an initial decrease in membrane permeability and a subsequent recovery of the permeability as the protein concentration drops. The final permeability is similar to the starting permeability, indicating minimal fouling during the run.

Figure 18:
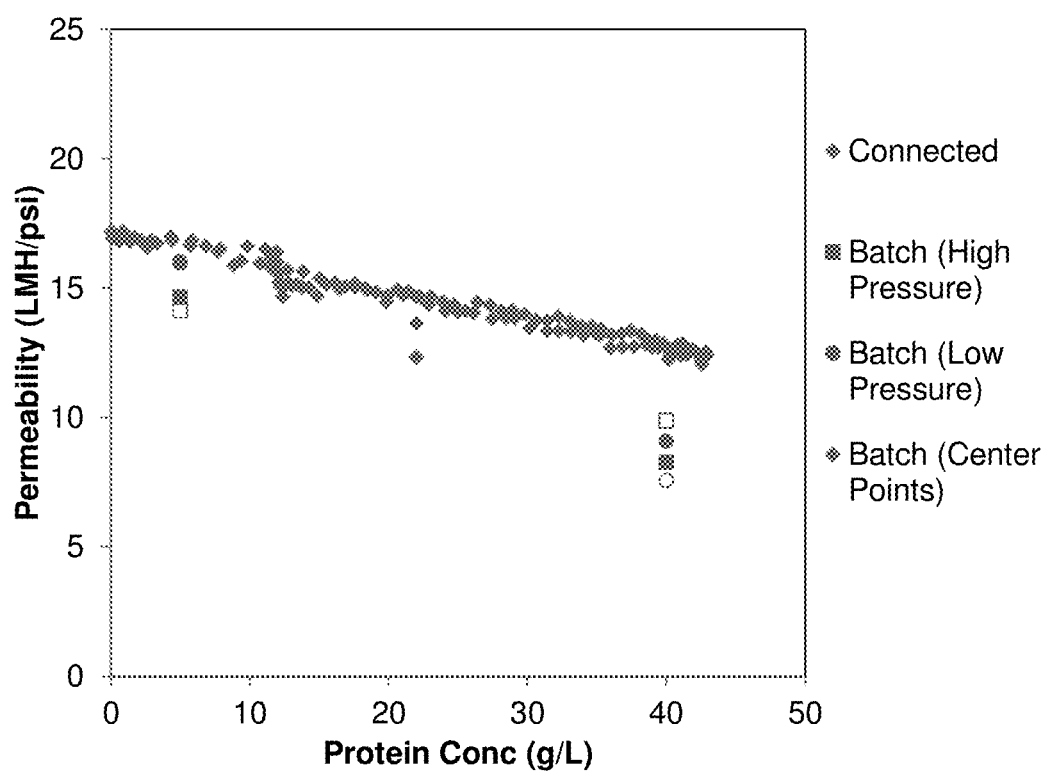
FIG. 18 is a graph illustrating a comparison of VF permeability trends for batch vs. connected (CEX-VF) mode using VPF-VPro with mAb C (in 0.1M NaAcetate pH 5, wherein connected data are shown clustered along a diagonal line, and batch data are shown with squares, circles and diamonds positioned below the clustered line, wherein the batch data are shown as the average VPro permeability for each independent experiment: squares indicate high pressure, circles low pressure and diamonds center points, and open shapes represent the low salt condition while filled shapes represent the high salt condition.

Results comparing the viral filter performance in connected and batch mode are shown in FIG. 18. Both sets of experiments were conducted with mAb C using the VPF and VPro filters. A batch factorial design experiment with 10 runs (duplicates with 2 center points) was conducted at a protein concentration of 5 or 40 g/L, sodium chloride concentration of 0 or 250 mM, and pressure of 15 or 45 psi, with duplicate center points at the mid-point of those parameters. The connected experiment was performed similarly to the one illustrated in FIG. 17a, with the data transformed to show VPro permeability as a function of the instantaneous protein concentration. The batch conditions were chosen to encompass the range of conditions seen in the connected process (FIG. 17a). The batch results indicate that salt concentration and pressure within the tested ranges have little impact on permeability, whereas increasing protein concentration shows a clear trend of decreasing permeability. Results from the connected experiments followed a similar permeability trend as the batch experiments, however, the filter permeability in batch mode was lower overall than the permeability in connected mode. These results are not unexpected, given that concurrent operation of the CEX and VF steps minimizes the duration that the CEX pool is held and thus minimizes formation of viral filter fouling components. These results demonstrate that batch experiments can provide directional trending on the relative impact of operating parameters, as well as an initial indication of minimum expected membrane permeability as a function of protein concentration. Ultimately, a representative connected run should be used for final process specification.

Once the hydraulic membrane permeability characteristics of the viral filter have been determined, the viral filter area can be sized appropriately for the connected process. The flow rate through the viral filter is predetermined by the flow rate set point of the prior chromatography step. Since the mode of operation is constant flow, the sizing of the viral filter is based on maintaining the feed pressure below a specified maximum limit. The limit may be dictated by the virus filter, the prefilter, or even the operating system. For example, the maximum pressure limit of the VPro filter set by the manufacturer is 60 psi and the VPF is 50 psi, therefore an operating pressure limit of 40-45 psi on the viral filter may need to be imposed in order to meet the prefilter limit. Experiments conducted in batch or connected mode can supply a minimum expected permeability based on the maximum expected protein concentration. With known inputs for flow rate, maximum pressure, and minimum permeability, the viral filter area can be calculated using Equation 1. Viral filter sizing for various connected processes is illustrated in FIG. 20, Table 2.

In a discrete viral filtration process, robustness is assessed by evaluating variations in feed composition within normal operating ranges. One parameter in the connected process that can affect the feed profile loaded onto the viral filter is the residence time of the surge vessel preceding the viral filter Minimizing the surge vessel residence time would result in an almost direct propagation of the preceding chromatography elution profile onto the viral filter. In contrast, maximizing surge vessel residence time would result in collection of the entire chromatography elution pool, and thus essentially render the viral filtration step a discrete operation. An experiment was conducted to compare surge vessel residence times of 5 and 25 minutes (FIGS. 17a and 17b, respectively). As expected, the short residence time corresponds to the maximum observed peak variation, whereas the long residence time produces a relatively homogenous pool.

Development of a Connected Tangential Flow Filtration Step

As described in the introduction, one control strategy that can be used to connect preceding downstream unit operations to the tangential flow filtration (TFF) step is a Constant Flow Strategy in which both the TFF retentate tank volume and the permeate flux are maintained constant during the entire connected operation. Mass accumulates in the TFF retentate tank during the course of connected processing, and the highest protein concentration is reached when all of the mass is in the TFF retentate tank at the end of the connected process. In order to maintain a constant permeate flux at the end of the connected process, the TFF retentate volume setpoint and membrane area need to be specified to accommodate the connected inlet flow rate and highest expected protein concentration. Bench-scale flux excursion studies are performed to map out the response of TFF permeate flux to varying feed crossflow rates, transmembrane pressures (TMP), and feed concentrations, and fit model parameters to the stagnant film model (Equation 2). This model can be used to calculate the specified parameters for the connected process.

Figure 19:
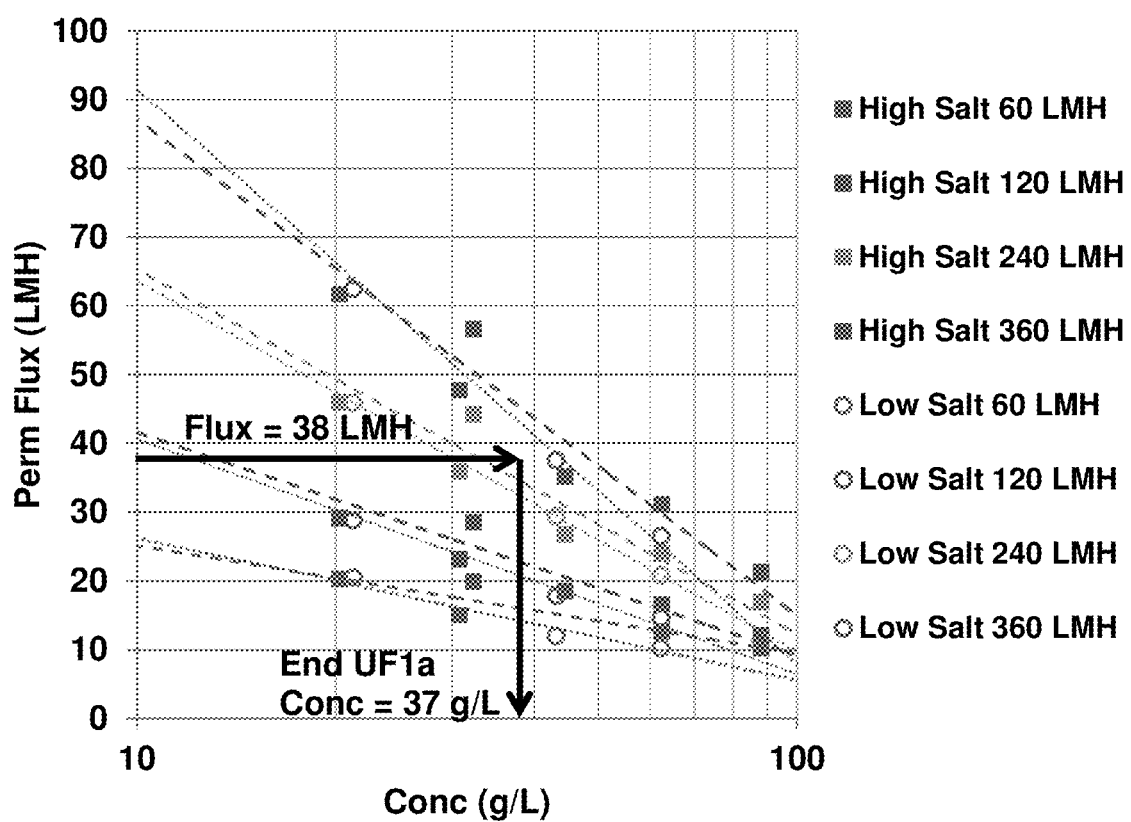
FIG. 19 is a graph illustrating TFF permeate flux vs. concentration at 20 psi TMP for low and high salt conditions with mAb C (in 100 mM acetate pH 5 with low salt 30 mM NaCl in open symbols or high salt 150 mM NaCl in closed symbols), wherein data points are indicated by symbols, lines indicate model fit, and arrows demonstrate the feed crossflow ramping required to maintain a constant permeate flux of 38 LMH through the end of the connected process (end of UF1a)

An example flux excursion dataset is shown in FIG. 19 for mAb C in salt buffer from the preceding unit operations. Flux excursions were performed with both a low salt (30 mM NaCl) and a high salt (150 mM NaCl) condition to evaluate the effect of variations in salt concentration due to the preceding CEX salt gradient elution. For this flux excursion study, a concentration range of 9-88 g/L was targeted with a TMP range of 5-20 psi and a feed cross flow range of 1-6 LMM; the 20 psi TMP data are shown in FIG. 19. The Pellicon 3 30 kDa regenerated cellulose membrane was used for this and subsequent examples. The results show comparable performance between the high and low salt conditions, indicating the performance of the TFF membrane is minimally impacted by variable salt concentration. This same trend has been observed for multiple molecules (data not shown). Permeate flux model parameters based on the high salt flux excursion data in FIG. 19 are: $k_o$=8.47, $C_w$=175, and n=0.73. For a connected process, Equations 2 and 3, along with the model parameters, can be used to calculate the TFF retentate volume setpoint based on known inputs for permeate flux (connected inlet flow/TFF area), maximum feed crossflow based on pump or system pressure limitations, and maximum expected mass. As described in the introduction section, the connected TFF process initiates once the setpoint retentate volume is reached. The feed crossflow and TMP are initially at a low setting in order to achieve the constant permeate flux target at the low protein concentration. As mass accumulates and the protein concentration increases, the feed crossflow and TMP ramp up to maintain the constant flux target, with the maximum feed crossflow maintained below the system limits. The ramping of the feed crossflow is conceptually illustrated by the arrows overlaid in FIG. 19; at a constant permeate flux of 38 LMH, the feed crossflow would initiate around 120 LMH and end around 300 LMH at the end of the connected process (end of UF1a). The targeted end of UF1a protein concentration for various connected processes, calculated using the stagnant film model parameters for each molecule process (not shown) and Equation 2, is shown in FIG. 20, Table 2.

Once the initial fill volume parameter is determined for the TFF step, the remainder of the unit operation development, such as the diafiltration and overconcentration/product recovery steps, is the same as for a standard batch TFF process, and therefore is not covered in this discussion. Process robustness for the connected portion of the TFF step can be assessed in multiple ways. The effect of variations in expected mass or protein concentration, feed crossflow, TMP, and inlet flow can be studied via a sensitivity analysis, using model fitted parameters and variations in input conditions. Generally, a safety factor should be used to allow for variations in the input conditions and still maintain a constant permeate flux, i.e. setting a more conservative or higher retentate volume setpoint specification. The permeate flux can also be influenced by the inherent membrane permeability and temperature of operation; experiments can be conducted around these input parameters.

Process Monitoring

Compared to discrete mode, unit operations in the connected process require additional process monitoring to facilitate unit operation transitions, help with pressure control, and provide necessary information about the performance of the run itself. Surge tank level monitoring provides critical transition signals which are communicated in real-time to the corresponding unit operation. For example, when the post-CEX chromatography surge tank level reaches its predetermined value, the control system sends this signal to the flowthrough chromatography skid to start the loading from the surge tank. When the post-CEX chromatography surge tank level reaches zero, the loading phase on the flowthrough skid stops and the wash phase starts. For the viral filtration step, the operation is performed at constant flow and the filter inlet pressure is monitored. The inlet pressure fluctuates when the product peak concentration passes through the viral filter. If the maximum pressure limit is reached, this triggers the control system to reduce the viral filtration flow rate and allow the flowthrough surge tank level to increase. In the TFF step, the permeate flow rate is measured by a flow meter during the connected process which not only provides flux information, but is also in communication with the control system to maintain the permeate flux at the pre-set value by adjusting feed crossflow rate and TMP. In addition, the control system monitors the TFF retentate tank level and maintains a constant volume by modulating the inlet or viral filtration step flow rate.

Step yield information for a discrete process is normally obtained by measuring the product concentration of the entire homogenous product pool and comparing it to the homogenous feed, along with the corresponding volumes. Since the concurrent operation of the connected unit operations does not allow for the entire pool to be collected, a small split stream is drawn from the main product stream during pool collection. This pseudo pool then provides samples for concentration measurement and product quality assays. Yield information can also be obtained real-time on the skid by integration of the UV A280 nm or A300 nm signal and using an experimentally determined product-specific extinction coefficient. The UV integration method can be used on the VF step immediately preceding the TFF step to calculate the accumulated mass in the TFF retentate tank at the end of the connected process. This accumulated mass is equivalent to the TFF load mass when operated in discrete mode, which is the key parameter for determination of retentate tank volume levels for diafiltration and overconcentration.

Large-Scale Performance

As described in the previous sections, each unit operation in the connected process is primarily developed in discrete mode and then connected together at bench scale for testing and further optimization. The process is then scaled-up and transferred into a pilot plant for demonstration and confirmation. Table 2 lists run parameters for 5 different molecules using the connected process CEX-AEX(FT)-VF-UF and its variations that have been successfully executed in a pilot plant. Surge tanks are located between chromatography steps and in front of the VF, with a size of 100 L, and operated at a residence time setpoint of 5-7 minutes. The yields listed in FIG. 20, Table 2 have been demonstrated at pilot-scale and are comparable to operation in discrete mode (discrete data not shown).

Figure 21A:
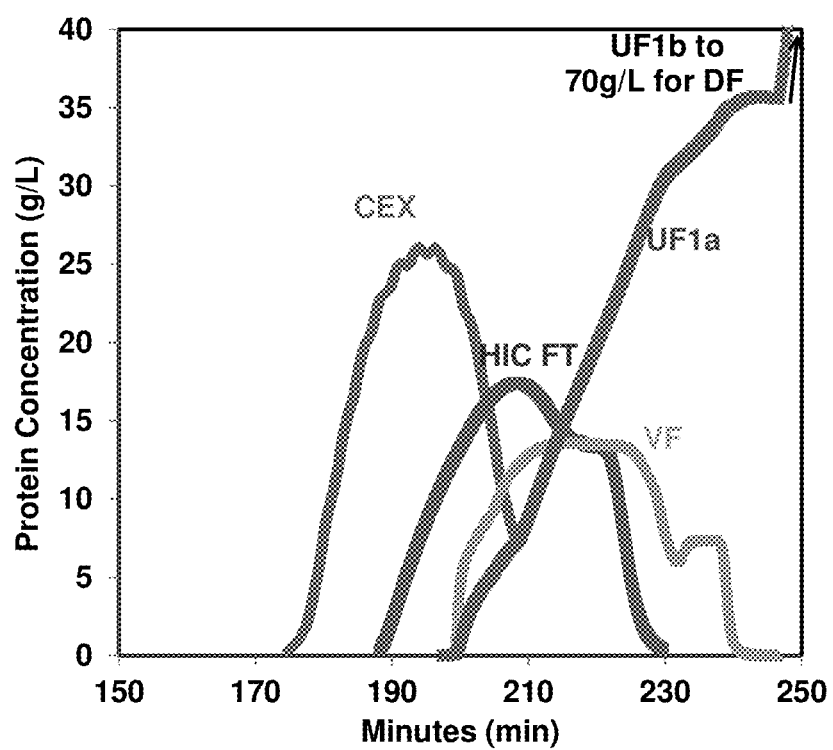
FIG. 21a is a graph of data illustrating a progression of mass through the mAb B connected downstream process with the following steps in order of operation: CEX bind/elute chromatography (CEX), HIC flowthrough chromatography (HIC FT), viral filtration (VF), and TFF (UF1a), wherein the connected portion of the process ends at UF1a; UF1b, DF, and OC are operated in discrete mode.

An example of the operational trends are shown in FIG. 21 for the mAb B connected downstream process (CEX-HIC(FT)-VF-UF). FIG. 21a shows the time progression of product mass through the connected downstream process over 70 minutes. The remainder of the UF step is performed in discrete mode, and during this time, the other unit operations complete their cleaning and equilibration steps to prepare for the next connected cycle. The concentration profile for the HIC(FI) and VF steps correspond to the elution peak from the CEX step, with a lower concentration at the HIC(FT) step due to an inline titration/dilution of the load, and a slightly lower concentration at the VF step due to line hold-up and surge tank mixing volumes. The later portion of the concentration profile for the HIC(FT) and VF steps levels off; this represents the stage of operation when the preceding connected unit operation has completed and the surge tank is being drained.

Figure 21B:
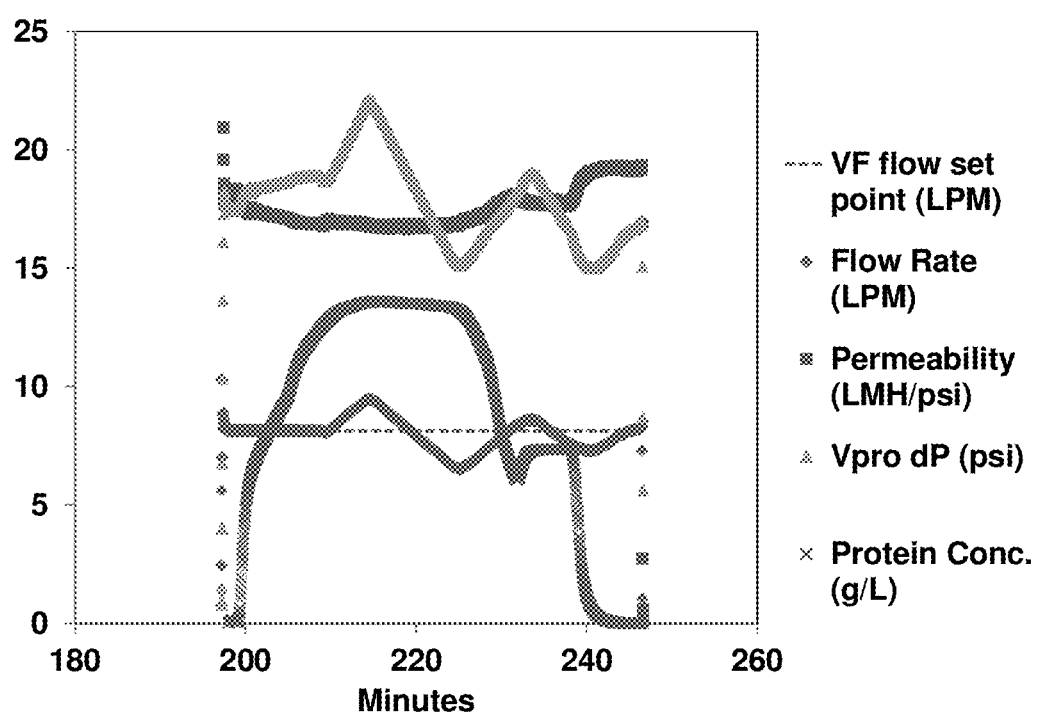
FIG. 21b is a graph of data illustrating a connected viral filtration trend, wherein flow variations (diamonds) around the setpoint (dashed line), and hence pressure drop (triangles) across the Viresolve Pro are a result of automation level control for the TFF retentate tank, and the dip in VPro filter permeability (squares) corresponds to the increase in peak protein concentration (Xs) on the filter.

FIG. 21b shows the connected VF profile, including flow set point, flow rate, permeability, Vpro pressure drop (dP) and protein concentration. The VF flow rate was set at 8.1 L/min, corresponding to the flow from the HIC(FT) step, however once the UF step was initiated, the VF flow rate was allowed to vary from its setpoint to maintain a constant UF retentate tank level (FIG. 21b). The pressure drop across the VF corresponds to the flow rate variation, but when the flow rate is normalized by the pressure drop, the filter permeability profile is relatively flat. There is a slight dip in the permeability as the protein concentration increases on the filter, and then it recovers to the initial permeability as the protein concentration decreases.

Figure 21C:
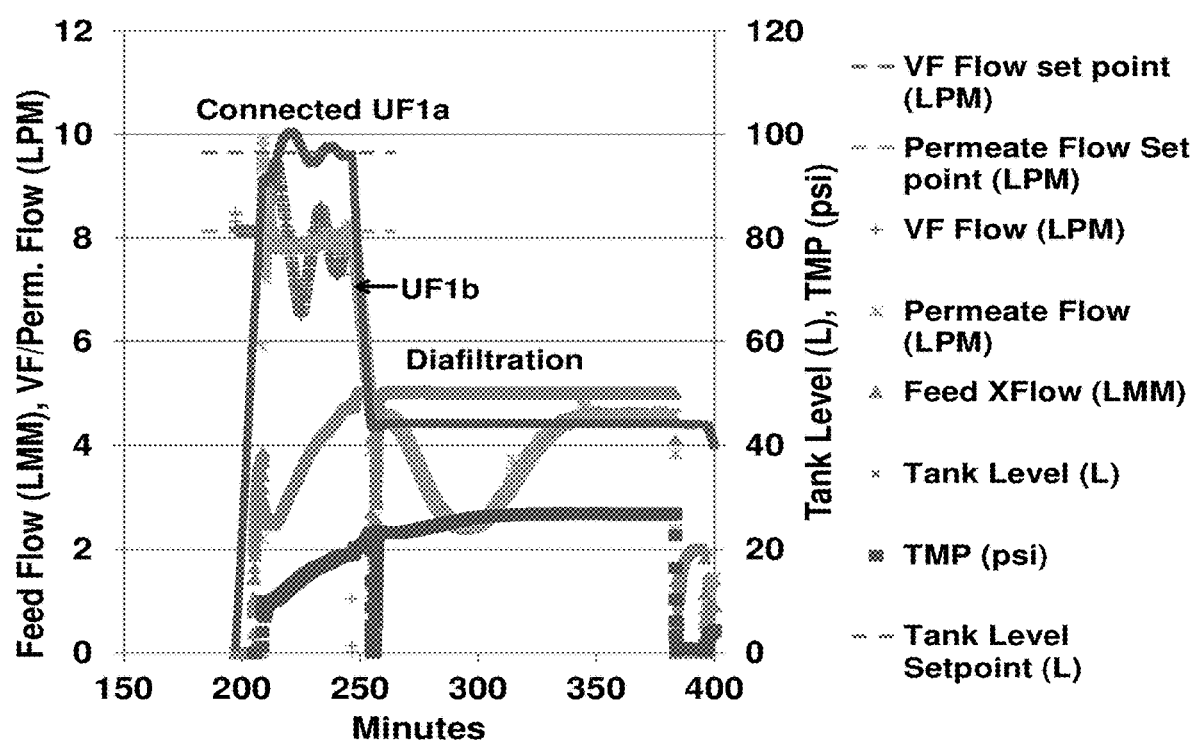
FIG. 21c is a graph of data illustrating a connected TFF trend (run parameters shown in FIG. 20, Table 2), wherein feed crossflow (triangles) and TMP (squares) increase during UF1a to maintain constant permeate flow rate (*s), and VF flow rate set point and TFF Permeate flow rate set points are matched and represented by the horizontal dashed line positioned slightly above 8 LPM, and slight oscillation in VF flow rate (+s) and TFF tank level (Xs) are due to automation control.

FIG. 21c shows the connected UF1a trend, as well as the discrete trends for the UF1b (batch concentration to DF set point) and DF stages of operation. As previously described, the VF flow rate varies around its setpoint to maintain the retentate tank level setpoint; the results of this process control can be observed in FIG. 21c. The UF permeate flow setpoint is the same as the VF flow setpoint, with the feed crossflow rate and TMP controlling the UF permeate flow. Both feed crossflow rate and TMP are observed to gradually increase as the protein concentration in the tank increases, and the control strategy is able to maintain the permeate flow rate at its setpoint.

Figure 22:
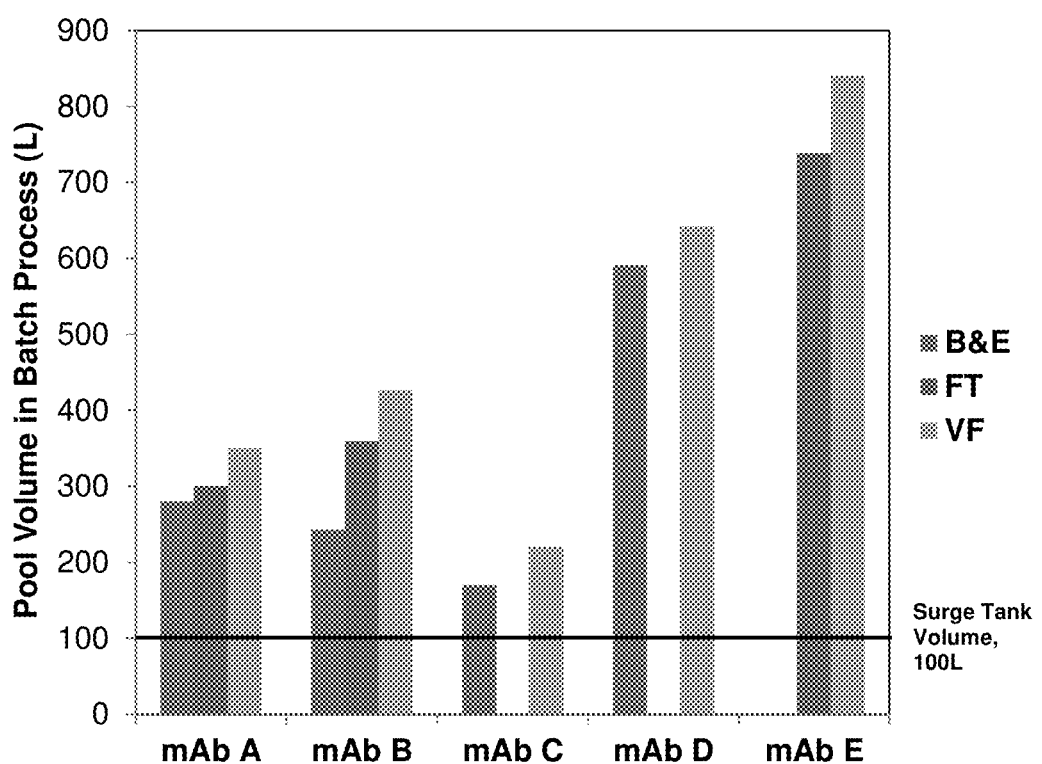
FIG. 22 is a graph showing projected pool volumes for the B/E (left-most vertical bar in each cluster of three), FT (middle vertical bar in each cluster of three), and VF (right-most vertical bar in each cluster of three) steps for mAb A-E operated in discrete mode compared to the connected process use of a 100 L surge tank.

As discussed in the introduction, one of the primary advantages to connecting downstream unit operations is the reduction in intermediate pool tank volumes, and thus footprint in the manufacturing plant. FIG. 22 illustrates a comparison of the tank volume requirements for a discrete process versus a connected process for each of the processes described in FIG. 20, Table 2. Since a manufacturing plant would need to design the pool tank size for the largest expected pool volume, the discrete processes would require at least a 1000 L tank. This is significantly larger than a 100 L surge tank operated with a 5-7 minute residence time for a connected process. In addition, the VF pool tank is completely eliminated in a connected process, since it can be directly connected to the UF retentate tank.

DISCUSSION AND CONCLUSIONS

The foregoing experimental work outlines the concept of a downstream process connected from the polishing chromatography steps through the final TFF step and demonstrates its successful execution at pilot scale. Multiple flow control strategies can be used to manage the flow disparity between unit operations, specifically the chromatography steps and variable permeate flow rate for the TFF step. A Constant Flow Strategy was proposed as a means to maintain a constant TFF permeate flow rate, and hence constant flow on the chromatography and viral filtration steps. This minimizes the number of dynamic effects that need to be studied during connected process development. This control strategy also results in constant surge tank and TFF retentate tank volumes throughout the course of connected operations, which allows for simpler process, equipment and automation design.

The development of the connected downstream process is similar in many respects to the development of a discrete process. Resin selection, viral and prefilter selection, and load conditions, such as pH, conductivity, and product concentration can all be studied through standard batch experiments. However, there are a number of unique aspects to consider in the development of a connected process. As one example, when the first connected step is a B/E chromatography step with a salt gradient elution, a shallower gradient slope may be beneficial to subsequent unit operations, such as the viral filter, to manage the peak product concentrations that propagate through the process. One advantage that can come with a shallower gradient slope is enhanced selectivity of impurity separation on the B/E chromatography step; there is flexibility in choosing a gradient slope based on process requirements rather than the constraint of a tank volume limitation. The first chromatography step is also critical in setting the flow rate for the entire connected process and therefore may need to be optimized in order to achieve a more economical sizing of the filtration steps. For the intermediate chromatography steps, the impact of a gradient elution needs to be assessed. Experiments should be conducted to study the effects of conductivity on step performance. While data was not presented in this paper, additional experiments may be performed to study the effects of variation in product concentration and impurity profile resulting from the gradient elution. Operational pH may also be screened, and in the event that the pH between unit operations is changed, an inline pH titration can be developed and implemented for connected processing.

The examples highlighted here illustrate the path for development of the connected filtration steps. Once the prefilter and viral filter are selected, and feed conditions are determined, relatively few connected process experiments are needed to determine filter sizing requirements and to assess robustness of the viral filter to variations in feed composition. For the TFF step, the development and implementation of an automated control strategy is necessary to manage a constant permeate flow operation, however, the development of the step can largely be accomplished through discrete experiments. Flux excursion studies performed at bench-scale, along with the corresponding flux model, are used to specify the parameters needed to operate the connected step in a constant flux mode. These can be directly applied to the scaled-up connected process, bypassing small-scale connected runs.

Additional processing monitoring capability must be considered for a connected process, for example, level control of the surge tanks to initiate and end the loading of the unit operations. Online UV integration can be implemented to determine the mass inputs for the TFF step, thus allowing volume targets to be set for diafiltration and overconcentration, and determination of step yield. A split stream pump also should be incorporated into the skid design to allow for the assessment of individual step performance and impurity clearance.

Processing an entire harvest lot requires multiple chromatography cycles in the connected process, with each connected cycle taking 1-2 hours, as described. Chromatography steps are normally cycled to reduce column size requirements and resin costs, and the TFF membrane is typically cleaned and reused, so the use of multiple cycles in a connected process for these steps is straightforward. In contrast, the viral filter is routinely employed for a single cycle of product loading followed by a single buffer flush in a discrete process. For a connected process, the loading on the viral filter is underutilized for a single connected cycle. The examples shown in FIG. 20, Table 2 indicate that loadings of 2-4 kg/m$^2$ are typical for a connected viral filtration step, whereas loadings of at least 20 kg/m$^2$ are achievable for this filter type (Bolton G, Basha J, LaCasse D. 2010. Achieving high mass-throughput of therapeutic proteins through parvovirus retentive filters. Biotech Progress 26(6):1671-1677). To improve the efficiency of viral filter use for connected processes, the same viral filter could be used for the entire harvest lot, with product loading phases followed by buffer flush phases for each successive cycle. The viral filter would experience alternating cycles of product and buffer, but the filter performance is expected to be governed by the total product loading from all cycles. Post-use filter integrity testing would be performed after all the cycles are completed to confirm that the filter is still integral. This approach provides significant benefits by reducing filter area requirements and thus cost of goods, eliminates time consuming installation and preparation steps associated with filter replacement, and minimizes the risk of adventitious agent introduction to the process stream by maintaining system closure after the viral filter. Since the complexity of plant scheduling and equipment utilization increases with multi-cycle connected processing, plant resource modeling will be required to ensure adequate facility fit within equipment turnaround time limitations. Additionally, assessing the viral clearance capability of the individual steps in a connected process, including cycling of the viral filter, warrants careful consideration. Aspects such as development of a qualified scaled-down model and introduction of the virus spike into a connected process will be addressed as the subject of a subsequent paper.

The connected downstream process presented here provides immediate benefits of pool tank volume reduction, thus leading to a more streamlined facility design. The reduction of tank size opens up the possibility of using mobile tanks which can be easily reconfigured for multiple products with different process requirements. This drives a reduction in capital costs and provides flexibility in manufacturing. An ultimate goal is to fully connect the harvest, protein A and downstream steps for fully continuous production. This would require the implementation of a continuous protein A capture step, utilizing sequential multi-column chromatography (SMCC) or simulated moving bed (SMB) technology, development of alternatives to the low pH viral inactivation batch operation, and implementation of all flowthrough polishing steps. This may be feasible in the near future, as evidenced by recent review articles focused on continuous production and process integration (Konstantinov K and Cooney C. 2014. White paper on continuous bioprocessing. J Pharm Sci DOI: 10.1002/jps.24268; Jungbauer A. 2013. Continuous downstream processing of biopharmaceuticals. Trends in biotechnology 31(8):479-492). The concepts and control strategies presented in this paper that connect the downstream polishing steps through the final TFF step move this technology another step closer to that goal.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

We claim:

1. A process control system comprising:
   (a) one or more filtration or purification processing units each operating at a flow rate, the one or more processing units comprising at least one of filtration or purification processing units;
   (b) a tank connected downstream from the one or more processing units;
   (c) a filter having an inlet, a permeate outlet, and a retentate outlet connected to the tank;
   (d) a feed pump having an inlet connected to the tank and an outlet connected to the inlet of the filter;
   (e) a sensor disposed at the permeate outlet to determine a flow rate at the permeate outlet; and
   (f) a control system that comprises one of the following configurations (i) through (iv):
   (i) the control system being coupled to the sensor and the one or more processing units, and adapted to control the flow rate through one or more of the one or more processing units according to the flow rate at the permeate outlet,
   (ii) the control system being coupled to the sensor and the feed pump, and adapted to control the feed pump according to the flow rate at the permeate outlet and to maintain a flow rate at the permeate outlet that is matched to the flow rate through one or more of the one or more processing units,
   (iii) the control system being coupled to the sensor and the feed pump, and adapted to control the feed pump according to the flow rate at the permeate outlet until a predetermined flow rate is reached for the feed pump, and to control the flow rate through one or more of the one or more processing units according to the flow rate at the permeate outlet after the predetermined flow rate is reached for the feed pump, or
   (iv) the control system being coupled to the sensor and the feed pump, and adapted to control the feed pump according to the flow rate at the permeate outlet until a predetermined flow rate is reached for the feed pump, and to permit a mismatch between the flow rate through the one or more processing units and the flow rate through the feed pump after the predetermined flow rate is reached for the feed pump.

2. The process control system according to claim 1, wherein the control system is (i) coupled to the sensor and the one or more processing units, and adapted to control the flow rate through one or more of the one or more processing units according to the flow rate at the permeate outlet.

3. The process control system according to claim 2, wherein the control system is adapted to decrease the flow rate through one or more of the one or more processing units according to a decrease in the flow rate at the permeate outlet.

4. The process control system according to claim 1, wherein the control system is (iii) coupled to the sensor and the feed pump, and adapted to control the feed pump according to the flow rate at the permeate outlet until a predetermined flow rate is reached for the feed pump, and to control the flow rate through one or more of the one or more processing units according to the flow rate at the permeate outlet after the predetermined flow rate is reached for the feed pump.

5. The process control system according to claim 4, wherein the predetermined flow rate is a maximum flow rate for the process control system.

6. The process control system according to claim 1, wherein the control system is (iv) coupled to the sensor and the feed pump, and adapted to control the feed pump according to the flow rate at the permeate outlet until a predetermined flow rate is reached for the feed pump, and to permit a mismatch between the flow rate through the one or more processing units and the flow rate through the feed pump after the predetermined flow rate is reached for the feed pump.

7. A process control method for use with a process control system comprising one or more filtration or purification processing units each having a flow rate, the one or more processing units comprising at least one of filtration or purification processing units, a tank connected to the one or more processing units, and a filter having an inlet, a permeate outlet, and a retentate outlet connected to the tank, the method comprising:
(a) sensing a flow rate at the permeate outlet; and
(b) performing one or more of the following (i) through (iv):
(i) controlling a flow rate through one or more of the one or more processing units and into the tank according to the flow rate at the permeate outlet,
(ii) pumping material from the tank into the filter according to the flow rate at the permeate outlet and matching the flow rate at the permeate outlet to the flow rate through one or more of the one or more processing units,
(iii) pumping material from the tank into the filter according to a flow rate at the permeate outlet until a predetermined pumping flow rate is reached, and subsequently controlling the flow rate through one or more of the one or more processing units once the predetermined pumping flow rate is reached, or
(iv) pumping material from the tank into the filter according to the flow rate at the permeate outlet until a predetermined pumping flow rate is reached, and subsequently pumping material from the tank into the filter according to the predetermined pumping flow rate thereby permitting a volume of material in the tank to vary.

8. The process control method according to claim 7, wherein (b)(i) is performed.

9. The process control method according to claim 8, wherein the flow rate through one or more of the one or more processing units is decreased according to a decrease in the flow rate at the permeate outlet.

10. The process control method according to claim 7, wherein (b)(iii) is performed.

11. The process control method according to claim 10, wherein the predetermined flow rate is a maximum flow rate for the process control system.

12. The process control method according to claim 7, wherein (b)(iv) is performed.

13. A process of purifying a protein utilizing a process control system comprising one or more upstream processing units each having a flow rate, a tank connected to the one or more upstream processing units, and a filter having an inlet, a permeate outlet, and a retentate outlet connected to the tank, the process comprising:
(a) sensing a flow rate at the permeate outlet while the protein flows from the retentate outlet back to the tank;
(b) performing one or more of (i) through (iv):
(i) controlling a flow rate through one or more of the one or more upstream processing units according to the flow rate at the permeate outlet, the flow rate being a flow rate of a material at least partly including the protein,
(ii) pumping a material at least partly including the protein from the tank into the filter according to the flow rate at the permeate outlet and matching the flow rate at the permeate outlet to the flow rate through one or more of the one or more upstream processing units,
(iii) pumping a material at least partly including the protein from the tank into the filter according to a flow rate at the permeate outlet until a predetermined pumping flow rate is reached, and subsequently controlling the flow rate through one or more of the one or more processing units once the predetermined pumping flow rate is reached, or
(iv) pumping a material at least partly including the protein from the tank into the filter according to the flow rate at the permeate outlet until a predetermined pumping flow rate is reached, and subsequently pumping material from the tank into the filter to according to the predetermined pumping flow rate thereby permitting a volume of material in the tank to vary; and
(c) purifying the protein in an eluate.

14. The process control method according to claim 13, further comprising formulating the protein in an excipient.

15. The process control method according to claim 13, wherein (b)(i) is performed.

16. The process control method according to claim 15, wherein the flow rate through one or more of the one or more upstream processing units is decreased according to a decrease in the flow rate at the permeate outlet.

17. The process control method according to claim 13, wherein (b)(iii) is performed.

18. The process control method according to claim 17, wherein the predetermined flow rate is a maximum system flow rate for the process control system.

19. The process control method according to claim 13, wherein (b)(iv) is performed.

* * * * *